:

US007108970B2

(12) United States Patent
Levinson

(10) Patent No.: US 7,108,970 B2
(45) Date of Patent: Sep. 19, 2006

(54) RAPID IDENTIFICATION OF CONDITIONS, COMPOUNDS, OR COMPOSITIONS THAT INHIBIT, PREVENT, INDUCE, MODIFY, OR REVERSE TRANSITIONS OF PHYSICAL STATE

(75) Inventor: Douglas Levinson, Sherborn, MA (US)

(73) Assignee: Transform Pharmaceuticals, Inc., Waltham, MA (US)

( * ) Notice: Subject to any disclaimer, the term of this patent is extended or adjusted under 35 U.S.C. 154(b) by 261 days.

(21) Appl. No.: 09/994,585

(22) Filed: Nov. 27, 2001

(65) Prior Publication Data

Related U.S. Application Data

(63) Continuation-in-part of application No. 09/756,092, filed on Jan. 8, 2001, and a continuation-in-part of application No. PCT/US01/00531, filed on Jan. 8, 2001.

(60) Provisional application No. 60/253,629, filed on Nov. 28, 2000, provisional application No. 09/994,585, provisional application No. 60/221,539, filed on Jul. 28, 2000, provisional application No. 60/196,821, filed on Apr. 13, 2000, provisional application No. 60/175,047, filed on Jan. 7, 2000.

(51) Int. Cl.
*C12Q 1/68* (2006.01)

(52) U.S. Cl. ............... 435/6; 435/DIG. 2; 435/DIG. 9; 356/301; 356/322; 356/364

(58) Field of Classification Search .................... 435/6, 435/DIG. 2, DIG. 9
See application file for complete search history.

(56) References Cited

U.S. PATENT DOCUMENTS

| | | | |
|---|---|---|---|
| 3,899,011 A | 8/1975 | Curtiss | |
| 3,932,131 A | 1/1976 | Rolfo-Fontana | |
| 4,399,687 A | 8/1983 | Collins | |
| 4,835,711 A | 5/1989 | Hutchins et al. | |
| 4,877,745 A | 10/1989 | Hayes et al. | |
| 5,417,923 A | 5/1995 | Bojanic et al. | |
| 5,445,934 A | 8/1995 | Fodor et al. | |
| 5,463,564 A | 10/1995 | Agrafiotis et al. | |
| 5,574,656 A | 11/1996 | Agrafiotis et al. | |
| 5,658,802 A | 8/1997 | Hayes et al. | |
| 5,684,711 A | 11/1997 | Agrafiotis et al. | |
| 5,744,305 A | 4/1998 | Fodor et al. | |
| 5,763,278 A | 6/1998 | Sickinger et al. | |
| 5,776,348 A * | 7/1998 | Selengut et al. | ............ 210/698 |
| 5,807,522 A | 9/1998 | Brown et al. | |
| 5,832,182 A | 11/1998 | Zhang et al. | |
| 5,843,767 A | 12/1998 | Beattie | |
| 5,859,703 A | 1/1999 | Aldridge et al. | |
| 5,901,069 A | 5/1999 | Agrafiotis et al. | |
| 5,928,952 A | 7/1999 | Hutchins et al. | |
| 5,956,137 A | 9/1999 | Lim et al. | |
| 5,999,255 A | 12/1999 | Dupee et al. | |
| 6,003,029 A | 12/1999 | Agrawal et al. | |
| 6,100,901 A | 8/2000 | Mohda et al. | |
| 6,140,643 A | 10/2000 | Brown et al. | |
| 6,175,816 B1 | 1/2001 | Flavin et al. | |
| 6,267,935 B1 * | 7/2001 | Hol et al. | ................ 422/245.1 |
| 6,296,673 B1 | 10/2001 | Santarsiero et al. | |
| 6,297,935 B1 | 10/2001 | Yoo et al. | |
| 6,327,334 B1 | 12/2001 | Murray | |
| 6,331,440 B1 | 12/2001 | Nordstedt et al. | |
| 6,333,501 B1 | 12/2001 | Labrenz | |
| 6,421,553 B1 | 7/2002 | Costa et al. | |
| 6,434,490 B1 | 8/2002 | Agrafiotis et al. | |
| 6,487,523 B1 | 11/2002 | Jarman et al. | |
| 2001/0016631 A1 | 8/2001 | Freitag et al. | |
| 2001/0036640 A1 | 11/2001 | D'Amico | |
| 2001/0055775 A1 | 12/2001 | Shultz et al. | |
| 2002/0023507 A1 | 2/2002 | Hajduk et al. | |
| 2002/0029621 A1 | 3/2002 | Hajduk et al. | |
| 2002/0032531 A1 | 3/2002 | Mansky et al. | |
| 2002/0037647 A1 | 3/2002 | Hwang et al. | |
| 2002/0183938 A1 | 12/2002 | Kobylecki et al. | |
| 2003/0022234 A1 | 1/2003 | Cawse et al. | |
| 2003/0033088 A1 | 2/2003 | Agrafiotis et al. | |
| 2003/0119060 A1 | 6/2003 | Desrosiers et al. | |
| 2003/0124028 A1 | 7/2003 | Carlson et al. | |
| 2003/0124610 A1 | 7/2003 | Kvanheim et al | |
| 2003/0219906 A1 | 11/2003 | Giaquinta et al. | |

FOREIGN PATENT DOCUMENTS

| | | |
|---|---|---|
| EP | 0553 539 | 10/1992 |
| EP | 0 807 811 | 4/1997 |
| EP | 0 882 500 | 10/1997 |

(Continued)

OTHER PUBLICATIONS

Leskovar, P.; Vogel, E.; Rozehnal, A. Urolithiasis Relat. Clin. Res., [Proc. Int. Symp.] 5th (1985), Meeting Date 1984, 627-30.*

(Continued)

*Primary Examiner*—Andrew Wang
*Assistant Examiner*—Jon D. Epperson
(74) *Attorney, Agent, or Firm*—Saliwanchik, Lloyd & Saliwanchik

(57) ABSTRACT

The invention concerns arrays comprising hundreds, thousands, to hundreds of thousands of samples and methods for screening thereof. These methods are useful to optimize, select, and discover compounds, compositions, or conditions that prevent, inhibit, induce, modify, or reverse physical-state transitions, particularly in-vivo physical-state transitions relating to disease causing processes. Such compounds, compositions, or conditions can be exploited to treat (e.g., reverse) or prevent the disease itself, the cause of the disease, or the symptoms of the disease.

25 Claims, No Drawings

FOREIGN PATENT DOCUMENTS

| | | | |
|---|---|---|---|
| EP | 0 921 396 | | 11/1998 |
| EP | 1 174 183 | | 8/1999 |
| EP | 1 174 185 | | 7/2001 |
| EP | 1 186 892 | | 8/2001 |
| WO | 94/11489 | | 5/1994 |
| WO | 96/06842 | | 3/1996 |
| WO | 96/16078 | | 5/1996 |
| WO | 98/40159 | | 9/1998 |
| WO | 98/47613 | | 10/1998 |
| WO | 98/52614 | | 11/1998 |
| WO | 99/04247 | | 1/1999 |
| WO | 99/06814 | | 2/1999 |
| WO | 99/08112 | | 2/1999 |
| WO | 99/45379 | | 9/1999 |
| WO | 99/45389 | | 9/1999 |
| WO | 00/03240 | | 1/2000 |
| WO | 00/29987 | | 5/2000 |
| WO | WO 01/51919 | * | 1/2001 |
| WO | 01/34290 | | 5/2001 |
| WO | WO 01/51919 | * | 7/2001 |
| WO | 02/31477 | | 4/2002 |
| WO | 03/014732 | | 2/2003 |

OTHER PUBLICATIONS

Klein, J.; Lehmann, C. W.; Schmidt, H.-W.; Maier, W. F. "Combinatorial Material Libraries on the Microgram Scale with an Example of Hydrothermal Synthesis" Angew. Chem. Int. Ed. 1998, 37(24), 3369-3372.*

Jandeleit, B.; Schaefer, D. J.; Powers, T.S.; Turner, H.W.; Weinberg, W. H. "Combinatorial Materials Science and Catalysis" Angew. Chem. Int. Ed. 1999 38, 2495-2532.*

Emiabata-Smith, D. F., Crookes, D. L.; Owen, M.R. "A practical approach to accelerated process screening and optimization" Organic Process Research & Development 1999, 3, 281-288.*

Findlay, W. P.; Bugay, D. E. "Utilization of Fourier transform-Raman spectroscopy for the study of pharmaceutical crystal forms" Journal of Pharmaceutical and Biomedical Analysis 1998, 16, 921-930.*

Addadi, "Growth and dissolution of organic crystals in the presence of organic crystals in the presence of additives stereochemistry and materials science" *Angew. Chem.*, 1985, vol. 97, pp. 476-496.

Beiswanger et al. "The Prevalence and Incidence of Dental Calculus in Adults" *J. Clin. Dent.*, 1989, vol. 1, pp. 55-58.

Berkovitch-Yellin et al. "Morphology Engineering of Organic Crystals with the Assistance of 'Tailor-Made' Growth Inhibitors" *North Western Branch Papers*, 1985, No. 3, pp. 1.1-1.22.

Fleisch et al., "Influence of Pyrophosphate on the Transformation of Amorphous to Crystalline Calcium Phosphate" *Calc. Tiss. Res.*, 1968, vol. 2, pp. 49-59.

Gadamasetti, K.G. (editor), *Process Chemistry in the Pharmaceutical Industry*, Marcel Dekker, Inc., N.Y., N.Y., 1999, pp. 372-388.

Mandel and Gaffar "Calculus revisited: A review" *J. Clin. Periodontol.*, 1986, vol. 13, pp. 249-257.

Popovitz-Biro et al. "Self-Organization of Molecules en Route to Crystal Formation," *From Simplicity Complexity Chem.—Beyond*, Pt. 1,1996, pp. 85-98.

Reixach, et al. "Inhibition of β-Amyloid-Induced Neurotoxicity by Imidazopyridoindoles Derived from a Synthetic Combinatorial Library" *J. Struct. Biol.*, 2000, vol. 130, pp. 247-258.

Suomi et al. "A Clinical Trial of a Calculus-Inhibitory Dentifrice," *J. Periodontol.*, 1974, vol. 45, No. 3, pp. 139-145.

Tabak et al., "Role of Salivary Mucins in the Protection of the Oral Cavity" *Journal of Oral Pathology*, 1982, vol. 11, pp. 1-17.

Toto and Rapp "A Clinical Comparison of a New Low Abrasive Dentifrice with Intermediate and High Abrasive Dentifrices" *J. Periodontol.*, 1972, vol. 43, No. 8, pp. 492-494.

Weissbuch et al. "Application of Cryo-Electron Microscopy to Self-Assembled Mixed Monolayers for Studying Crystallinity and Twinning" *J. Phys. Chem.*, 1993, vol. 97, pp. 8692-8695.

Weissbuch et al. "Mixed Monolayers for the Design of Structured Surfaces to Induce Oriented 3-D Crystallization" *J. Phys. Chem.*, 1993, vol. 97, pp. 12848-12857.

Weissbuch et al. "Structural Changes in Amphiphilic Aggregates at the Air-Solution Interfaces as Studied by Oriented Crystallization and Nonlinear Optics" *J. Am. Chem. Soc.*, 1990, vol. 112, pp. 5874-5875.

Weissbuch et al. "'Tailormade' Auxiliaries for Nucleation, Growth and Dissolution of Organic Crystals" *Pure and Appl. Chem.*, 1986, vol. 58, No. 6, pp. 947-954.

Weissbuch et al., "Towards an Understanding and Control of Nucleation, Growth, Habit, Dissolution, and Structure of Crystals Using 'Tailor-Made' Auxiliaries" *Molecular Modeling Applications in Crystallization*, edited by Allan S. Myerson, Cambridge University Press, 1999, pp. 166-227.

Zander et al. "Mineralization of Dental Calculus" *Proceedings of the Society for Experimental Biology and Medicine*, 1960, vol. 103, No. 2, pp. 257-261.

Aldridge, P.K. et al., "A Robotic Dissolution System with On-Line Fiber-Optic UV Analysis", *Journal of Pharmaceutical Sciences*, 84:8: (1995).

Andersen, G. et al., "A Spreadsheet Approach to Automated Protein Crystallization", *J. Appl. Cryst.*, 29:236-240 (1996).

Anquetil, P.A. et al., "Laser Raman Spectroscopic Analysis of Polymorphic Forms in Microliter Fluid Volumes", *Journal of Pharmaceutical Sciences*, vol. 92:1: 149-160 (2003).

Beckmann, W. et al., "The Effect of Additives on Nucleation: A Low Cost Automated Apparatus", *Journal of Crystal Growth*, 99:1061-1064 (1990).

Bowtell, David D., "Options Available—from Start to Finish—for Obtaining Expression Data by Microarray", Nature Genetics Supplement, vol. 21, Jan. 1999.

Brodersen, D. et al., "XAct: a program for construction, automated setup and bookkeeping of crystallization experiments", *Journal of Applied Crystallography*, 32:1012-1016 (1999).

Bugay, David E., "Characterization of the Solid-State: Spectroscopic Techniques" Advanced Drug Delivery Reviews 48 (2001) 43-65.

Bullock, E. & Pyatt, E.C., "Apparatus for the growth of crystals from small volumes of solution", *Journal of Physics E- Scientific Instruments*, vol. 5: 412-413 (1972).

Carrie, T. et al., "An Automated Sampling Device for Dissolution Testing", Journal of Pharm. Sciences, vol. 72, No. 8, Aug. 1983.

Casay, G. et al., "Laser scattering in a hanging drop vapor diffusion apparatus for protein crystal growth in a microgravity environment", *J. of Cryst. Growth*, 122:95-101 (1992).

Chayen, N. et al., "An Automated System for Micro-Batch Protein Crystallization and Screening", *J. App. Cryst.*, 23:297-302 (1990).

Chayen, N. et al., "New Developments of the IMPAX Small-Volume Automated Crystallization System", *Acta Cryst.*, D50:456-458, (1994).

Chayen, N. et al., "Microbatch Crystallization under Oil—A New Technique Allowing Many Small-Volume Crystallization Trials", Journal of Crystal Growth 122 (1992) 176-180.

Cheung, Vivian et al., "Making and Reading Microarrays" Nature Genetics Supplement, vol. 21, Jan. 1999.

Cox, J. et al., "Experiments with Automated Protein Crystallization", *J. Appl. Cryst.*, 20:366-373 (1987).

Cox, M. J. et al., "An Investigation of Protein Crystallization Parameters Using Successive Automated Grid Searches", Journal of Crystal Growth, 90 (1988) Jul. Nos. 1-3 Amsterdam.

Creese, Ian, "Receptor Binding as a Primary Drug Screen", *Neurotransmitter Receptor Binding* 2nd Ed. 1995.

Cudney, B. et al., "Screening and Optimization Strategies for Macromolecular Crystal Growth", *Acta Cryst.*, D50:414-423, (1994).

Davis, G.F. et al., "Comparison of High Throughput Screening Technologies for Luminescence Cell-Based Reporter Screens", *Journal of Biomolecular Screening*, vol. 7: No. 1, (2002).

Eckstein, RJ et al, "Unattended, Robotic Drug-release Testing of Enterically Coated Aspirin", Anal. Chem. 1986, 58, 2316-2320.

Findlay, W. Paul et al., "Utilization of Fourier Transform-Raman Spectroscopy for the Study of Pharmaceutical Crystal Forms", Journal of Pharm. And Biomedical Analysis, 16 (1998) 921-920.

Fodor, Stephen P., "Massively Parallel Genomics", SCIENCE Magazine, vol. 277, Jul. 15, 1997 pp. 393-394.

Food and Drug Administration, 1997, "International Conference on Harmonisation; Draft Guideline on Impurities: Residual Solvents; Availability", Federal Register 62:24302-24309.

Gilliland, G. et al., "Screening for Crystallization Conditions and Robotics", Acta Cryst., D50:408-413 (1994).

George, Ronald et al., "Automated Dissolution Testing of Sustained Release Tablets" American Laboratory, Feb. 1988.

Gold, Gerald et al., "Effects of Selected USP Talcs on Acetylsalicylic Acid Stability in Tablets", Journal of Pharm. Sciences, vol. 53, No. 1, Jan. 1964.

Gonzalez, F. et al., "Crocodile: An Automated Apparatus for Organic Crystal Growth From Solution", Acta Astronautica, 25:12:775-784 (1991).

Gordon, Eric M. et al., "Applications of Combinatorial Technologies to Drug Discovery. 2. Combinatorial Organic Synthesis, Library Screening Strategies, and Future Directions", Journal of Medicinal Chemistry, vol. 37, No. 10, May 13, 1994.

Jancarik, J. et al., "Fast Communications", J. of App. Cryst., 24: 409-411 (1991).

Kelders, H. et al., "Automated protein crystallization and a new crystal form of a substilisin: eglin complex", Protein Engineering, vol. 1:4:301-303, (1987).

Kuball, M., "Raman Spectroscopy of GaN, AlGaN and AlN for process and growth monitoring/control", Surface and Interface Analysis, 31:987-999 (2001).

Lamparter, E. et al., "The Automation of Dissolution Testing of Solid Oral Dosage Forms", Journal of Pharmaceutical & Biomed Analysis, vol. 10, Nos. 10-12, pp. 727-733, 1992.

Lenczewski, Melissa E. et al., "Automated Screening Method for Determining Optimum Preservative Systems for Personal and Home Care Products", Journal of AOAC International vol. 18, No. 3, 1998.

Lennernas, Hans, "Human Intestinal Permeability", Journal of Pharm Sciences, vol. 87, No. 4, Apr. 1998.

Lindsey, J. et al., "Robotic work station for microscale synthetic chemistry: On-line absorption spectroscopy, quantitative automated thin-layer chromatography, and multiple reactions in parallel", Rev. Sci, Instrum., 59:6:940-950(1998).

Littlechild, J.A., "Protein Crystallization: Magical or Logical: Can we Establish Some General Rules?", Journal of Physics D: Applied Physics 24 (1991) Feb. 14, No. 2, Bristol GB.

Lo, Su-Chin et al., "Automated Drug Dissolution Monitor that Uses a UV—Visible Diode Array Spectrophotometer", Journal of Pharm. Sciences, vol. 82, No. 4, Apr. 1993.

Luque de Castro, M.D. et al., "Automation of Pharmaceutical Dissolution Testing by Flow Injection Analysis", Journal of Pharm & Biomedical Analysis, vol. 8, No. 4, pp. 339-336 1990.

Mann, Mattthias, "Quantitative Proteomics?" Nature Biotechnology vol. 17, Oct. 1999.

Marshall, Andrew et al., "DNA Chips: An Array of Possibilities" Nature Biotechnology vol. 8, Jan. 1998.

Martin, PA et al., "Automation of Microtitier Plate-chromogenic Substrate LAL Endotoxin Assay Method by Use of a Modified Cetus Pro/Pette Express System" Journal of Parenteral Science & Technology, vol. 40, No. 2, Mar.-Apr. 1986.

Matousek et al., "Flourenscence Suppression in Resonance Raman Spectroscopy Using a High-Performance Picosecond Kerr Gate", Journal of Raman Spectroscopy 2001, 32: pp. 983-988.

McFarland, Eric W. et al., "Combinatorial Approaches to Materials Discovery", Tibtech Mar. 1999 (vol. 17) pp. 107-115.

McPherson, A., "Two approaches to the rapid screening of crystallization conditions", Journal of Crystal Growth, 122:161-167 (1992).

Morris, D. et al., "Automation of Protein Crystallization Trials: Use of a Robot to Deliver Reagents to a Novel Multi-Chamber Vapor Diffusion Plate", Biotechniques, vol. 7:5:522-527 (1989).

Morris, Kenneth R. et al., "An Integrated Approach to the Selection of Optimal Salt Form for a New Drug Candidate", International Journal of Pharmaceutics 105 (1994) 209-217.

Morris, Kenneth R. et al., "Theoretical Approaches to Physical Transformations of Active Pharmaceutical Ingredients during Manufacturing Processes", Advanced Drug Delivery Reviews 48 (2001) 91-114.

Newman, Alan, "Send in the Robots", Analy. Chem., 62:1:29-34 (1990).

Oldfield, T. et al., "A Flexible Approach to Automated Protein Crystallization", J. Appl. Cryst., 24:255-260 (1991).

Otsuka, Makoto et al., "Physicochemical Characterization of Glybuzole Polymorphs and their Pharmaceutical Properties", Drug Development and Industrial Pharmacy, 25 (2) 197-203 (1999).

Papas, Andrew N. et al., "Evaluation of Robot Automated Drug Dissolution Measurements" Analytical Chemistry, vol. 57, No. 7, Jun. 1985.

Persidis, Aris, "An Ambitious Drug Development Platform Attempts to Link Gene Sequence to Expressed Phenotype under Various Physiological States", Nature Biotechnology, vol. 16, Apr. 1995.

Ramsey, Graham,. "DNA Chips: State of the Art", Nature Biotechnology, vol. 16, Jan. 1998.

Rivas, Laura et al, "Conformation Study of AZT in Aqueous Solution and Adsorbed on a Silver Surface by Means of Raman Spectroscopy", Journal of Raman Spectroscopy, 2001, 33: 6-9.

Rosch, P. et al., "Chemotaxonomy of Mints of Genus Mentha by Applying Raman Sepectroscopy", Wiley InterScience—www.interscience.wiley.com DOI:10.1002/bip.10099 (2002).

Rubin, B. et al., "Minimal intervention robotic protein crystallization", Journal of Crystal Growth, 110: 156-163 (1991).

Shah, Ketan P. et al., "Automated Analytical Systems for Drug Development Studies 3. Multivessel Dissoulution Testing System Based on Microdialysis Sampling", Journal of Pharmaceutical and Biomedical Analysis 13 (1995) 1235-1241.

Shaw, P. et al., "Practical experimental design techniques for automatic and manual protein crystallization", Journal of Crystal Growth: 196:665-673, (1999).

Sobriano, T.M. et al., "ASTEC: an Automated System for Sitting-Drop Protein Crystallization," Journal of Applied Crystals, 26: 558-562 (1993).

Song, CX et al., "Controlled Release of U-8683 from Double-Layer Biodegradable Matrices: Effect of Additives on Release Mechanism and Kinetics", Journal of Controlled Release 45 (1997) 177-192.

Stephenson, Gregory A. et al., "Characterization of the Solid State: Quantitative Issues" Advanced Drug Delivery Reviews 48 (2001) 67-90.

Tisone, T., "Dispensing systems for miniaturized diagnostics", IVD Technology, 1998.

Van de Poll, S.W.E. et al., "In Situ investigation of the chemical composition of ceroid in human atherosclerosis by Raman spectroscopy", Journal of Raman Spectroscopy, 33:544-551 (2002).

Vippagunta, Sudha R. et al., "Crystalline Solids" Advanced Drug Delivery Reviews, 48 (2001) 3-26.

Ward, Keith B. et al., "Automatic Preparation of Protein Crystals Using Laboratory Robotics and Automated Visual Inspection", Journal of Crystal Growth 90 (1988) 325-339.

Wehrens, R., et al., "Mixture Modelling of medical magnetic resonance data", Journal of Chemometrics, 16:274-282 (2002).

Yakovlev, Y. et al., "A Laboratory Apparatus for Crystal Growth from Solution", Instruments and Experimental Techniques, vol. 41:2: 292-296 (1998).

Yu, Lian, "Amorphous Pharmaceutical Solids: Preparation, Characterization and Stabilization" Advanced Drug Delivery Reviews 48 (2001) 27-42.

Zhu, Haijian et al., "Influence of Water Activity in Organic Solvent + Water Mixtures on the Nature of Crystallizing Drug Phase. 1. Theophylline," International Journal of Pharmaceutics, 135 (1996) 151-160.

Zeelen, J. et al, "Crystallization Experiments with 2-Enoyl-CoA Hydratase, Using an Automated 'Fast-Screening' Crystallization Protocol", Acta Cryst., D50:443-447 (1994).

Craw, S. et al. "Case-based design for tablet formulation" XP-000934085, Zeneca Pharmaceuticals, UK pp. 358-369, 1998. (previously reference LD).

Ferwerda, R. et al. "The use of FT-Raman spectroscopy and chemometric procedures in the analysis of polymers" Nicolet Instrument Corporation, Application Note AN97100, pp. 1-2, 1997. (previously reference QD).

Fodor, S.P. et al. "Light-directed, spatially addressable parallel chemical synthesis" *Science* 251(499):767-773, 1991. (previously reference TD).

Petty, C. et al. "Applications of FT-Raman spectroscopy in the pharmaceutical industry", Nicolet Instruments Pamphlet. (previously references ZE), 11(5):41-45, 1996.

Petty, C. et al. "The use of FT-Raman spectroscopy in the study of formulated pharmaceuticals" Nicolet Instruments Application Note AN9262, pp. 1-4, 1995. (previously reference AF).

Shah, K. et al. "Automated analytical systems for drug development studies, II. A system for dissolution testing" *J. Pharm. & Biomed. Anal.* 12(12):1519-1527, 1994. (previously reference FF).

* cited by examiner

RAPID IDENTIFICATION OF CONDITIONS, COMPOUNDS, OR COMPOSITIONS THAT INHIBIT, PREVENT, INDUCE, MODIFY, OR REVERSE TRANSITIONS OF PHYSICAL STATE

1. RELATED APPLICATION

This application incorporates by reference, and claims priority from, the U.S. provisional application No. 60/253,629 filed on Nov. 28, 2000, entitled RAPID IDENTIFICATION OF CONDITIONS, COMPOUNDS, OR COMPOSITIONS THAT INHIBIT, PREVENT, INDUCE OR REVERSE TRANSITIONS OF PHYSICAL STATE. This, application is also a continuation-in-part of U.S. patent application Ser. No. 09/756,092, filed Jan. 8, 2001, pending, which claims the benefit of U.S. Provisional Patent Application 60/175,047, filed Jan. 7, 2000; U.S. Provisional Patent Application 60/196,821, filed Apr. 13, 2000; and U.S. Provisional Patent Application 60/221,539, filed Jul. 28, 2000. This application is also a continuation-in-part of International Application PCT/US01/00531, filed Jan. 8, 2001 which claims the benefit of U.S. Provisional Patent Application 60/175,047, filed Jan. 7, 2000; U.S. Provisional Patent Application 60/196,221, filed Apr. 13, 2000; and U.S. Provisional Patent Application 60/221,539, filed Jul. 28, 2000.

2. FIELD OF THE INVENTION

The invention is directed to methods and systems for high through-put sample screening for optimization of conditions and discovery of new compounds and compositions. In particular, the invention is directed to methods and systems for high-throughput, rapid screening of large numbers of samples for identification of conditions, compounds, or compositions that inhibit, prevent, induce, modify, or reverse transitions of physical state, particularly, where the physical-state transition relates to a disease process.

3. BACKGROUND OF THE INVENTION

Many serious diseases of both humans and animals are caused by abnormal physical-state transition of benign or beneficial substances, normally present in the body, such that a disease-causing substance results. Discovery of conditions, compounds, or compositions that prevent or inhibit formation or that reverse formation (e.g., promote dissolution or destruction) of such disease-causing substances is an important part of pharmaceutical development and research. Also important is discovery of compounds, compositions, or conditions that promote desirable physical-state transitions for reversal of disease processes, for example, reversal of osteoporosis by inducing formation of bone mass.

These so-called physical-state-transition disorders are a large and very heterogenous group of diseases. They include disorders caused by undesirable crystallization, bio-mineralization, polymerization, or calculus build up, such as bladder stones, kidney stones, gall stones, tartar build up on teeth, protein precipitation in body fluids, passage of aggregates based on their form or habit, and defects in bone formation or loss of bone mass. Polymerization, multimerization, and macro-molecular structures are significant in diseases, disorders, and conditions such as cancer and metastasis, allergy, e.g., due to IgE complexes, malarial parasite infections with sequestration of hematin, assembly of viral capsids and the like. Additionally, it is now known that structure or conformation changes of proteins are the cause or contribute to a range of very serious human diseases such as Alzheimer's disease, the amyloid diseases, and the prion diseases, such as Creutzfeldt-Jakob Disease.

The occurrence of these undesirable physical-state transitions can be influenced by the immediate environment. For example, the deposition of calcium phosphate in solid form can be inhibited by the presence of pyrophosphate, even if the local concentration of calcium and phosphate ion would promote such deposition. Likewise, the formation of solids in the urinary system can be altered by controlling the pH of the urine or by preventing nucleation. The tendency of protein to adopt a beta-pleated sheet conformation, typical of the amyloid diseases, is critically dependent on the precise environmental conditions.

3.1 Disease-Causing Physical-State Transitions in the Body

Formation of disease-causing substances can occur by many different mechanisms. In general, a physical-state transition is involved. For example, bio-precipitation and bio-crystallization processes, such as mineralization (crystallization and buildup of minerals) and calcification (crystallization of calcium salts). Disease-causing substances can also form by a physical-state shift from one solid to a more unfavorable solid, for example, a polymorphic shift. Crystallization is a physical-state change that results in the formation of a crystalline substance. The process of crystallization is one of ordering. During this process, randomly organized molecules in a solution, an amorphous substance, a melt, or the gas phase take up specific, ordered positions in a crystal matrix. The most common type of crystallization is crystallization from solution, for example, crystallization in bodily fluids.

The term precipitation is usually reserved for formation of amorphous substances that have no symmetry or ordering and cannot be defined by habits or as polymorphs. Bio-precipitation processes can result in organic deposits, such as plaques, fats, and other undesirable amorphous-substance buildup in the body. Both crystallization and precipitation result from the inability of a solution (e.g., body fluid) to fully dissolve the substance and can be induced by changing the state of the system in some way. Common parameters that can promote or discourage precipitation or crystallization include: pH; temperature; concentration; and the presence or absence of inhibitors or impurities.

A process akin to crystallization that is typically limited to formation of substances displaying local order is that of deposition or polymerization of proteins and other molecules resulting in deposits and other aggregates. Such aggregates result in disease state such as those seen in sickle cell disease with polymerization of hemoglobin that is rate limited by a nucleation step, a stochastic process, in manner similar to crystallization and precipitation. Additional examples include Huntington's chorea (caused by aggregates including the protein huntingtin), Parkinson's disease, and many other disorders.

Important processes in crystallization and precipitation are nucleation, growth kinetics, interfacial phenomena, agglomeration, and breakage. Nucleation results when the phase-transition energy barrier is overcome, thereby allowing a particle to form from a supersaturated solution. Growth is the enlargement of particles caused by deposition of solid material on an existing surface. The relative rate of nucleation and growth determine the size distribution. Agglomeration is the formation of larger particles through two or more particles (e.g., crystals) sticking together. The thermodynamic driving force for both nucleation and growth is supersaturation, which is defined as the deviation from thermodynamic equilibrium.

During crystallization or precipitation an adduct molecule can be incorporated into the matrix, adsorbed on the surface, or trapped within the particle or crystal. Such compositions are referred to as inclusions, such as hydrates (water molecule incorporated in the matrix) and solvates (solvent trapped within a matrix). Whether a crystal forms in the body as an inclusion can have a profound effect on the clinical aspects of a disease, such as ease of removal from the body. For example, inclusions may dissolve more or less readily in bodily fluids or have different mechanical properties or strength than the corresponding non-inclusion compounds.

Furthermore, the same compound can crystallize in different external shapes depending on, amongst others, the composition of the crystallizing medium. These crystal-face shapes are described as the crystal habit. Such information is important because the crystal habit has a large influence on the crystal's surface-to-volume ratio. Although crystal habits have the same internal structure and thus have identical single crystal- and powder-diffraction patterns, they can still exhibit different pharmaceutical properties (Haleblian 1975, *J. Pharm. Sci.*, 64:1269). Crystal size and shape of disease-causing substances have a great effect on the clinical aspects of a disease, such as irritation and inflammation. Thus discovering conditions or pharmaceuticals that affect crystal habit are needed.

Additionally, the same compound can crystallize as more than one distinct crystalline species (i.e., having a different internal structure and physical properties) or shift from one crystalline species to another. This phenomena is known as polymorphism and the distinct species known as polymorphs. Polymorphs can exhibit different optical properties, melting points, different solubility, different chemical reactivities, different dissolution rates, and different bioavailabilities. Factors that affect polymorphism of foreign substances in the body are of clinical importance. For example, one polymorph may be more readily removed from the body—e.g., easier to dissolve in body fluids—than another. Thus, conditions, compounds, or compositions that prevent shift to an unfavorable polymorph or promote shift to a more favorable polymorph are desirable.

Depending on concentrations, the presence of inhibitors or impurities, and other conditions, particles can form from solution in different sizes and size distributions. In general, smaller particles are more easily eliminated from the body and have higher surface-to-volume ratio that allows easier dissolution in bodily fluids. Thus, compounds or compositions that promote small crystal size can be of clinical importance in treating or preventing diseases caused by solid deposits in the body.

Disease-processes can also be induced by pathogenic degradations of substances in the body, for example, loss of bone mass caused by bone resorption or osteoporosis. Thus therapeutic compositions, compounds, or conditions that slow or reverse such processes are greatly needed.

Another instance of unfavorable biocrystallization or bioprecipitation concerns physiologically low-solubility pharmaceuticals or pharmaceuticals that complex with tissue or other bodily substances. Compounds that prevent or inhibit such crystallization or precipitation may have clinical applications, such as coadministration with the problematic pharmaceutical.

3.2 Diseases Caused by Physical-State Transitions in the Body

The following is a partial list of diseases caused by physical-state changes that result in deposition of disease-causing substances in the body for which the current invention can be used to find compounds, compositions, or conditions that inhibit or prevent such physical state changes. See, *Cecil Textbook of Medicine*, Eds. Goldman L. & Bennett J. C., 21$^{st}$ Edition (2000), W.B. Saunders Co., Philadelphia; *Primer on the Metabolic Bone Diseases and Disorders of Mineral Metabolism*, Second Edition, Ed. Favas, M. J. (1993), Lippincott-Raven Publisher, Philadelphia-New York, both incorporated by reference herein in their entirety.

3.2.1 Calcium Pyrophosphate Dihydrate Crystal Deposition Disease (Pseudogout Syndrome)

Calcium pyrophosphate dihydrate (CPPD) crystals may be deposited in joint spaces. Here they cause inflamation with pain and swelling and limitation of motion of the involved joint. These CPPD crystals are rod or rhomboid shapes 2–20 micrometers long, they are weakly birefringement crystals. Any joint can be involved but the most common are the knee, wrist and metacarpophalangeal joint. Acute attacks of pseudogout often occur in the knees and are incapacitating for days or weeks. The disease is most frequent in the elderly of both genders. The clinical presentation may be confused with gout hence its common name "pseudo gout syndrome". Unfortunately, no treatment is available to dissolve the crystal deposits.

3.2.2 Apatite Crystal Deposition Disease

Apatite crystal deposition is a common factor in bursitis and periarthritis. Most common areas of involvement are shoulders, hips, knees and digits. An extremely destructive arthritis may occur at the shoulder, "Milwaukee shoulder," or at hips and knees in elderly people. Other types of calcium phosphates such as octacalcium phosphate can be seen along with the apatite crystals.

The individual apatite crystals that form in this type of disease are very small and can be seen only by electron microscope. However, clumps of these crystals often form and appear as 2–25 MM shing (but not generally birefringent), globules in the light microscope and when seen are strongly suggestive of the diagnosis. Radiographs may show soft tissue calcifications with or without bone erosions. Definitive diagnosis of this type of crystal deposition disease can only be made by electron microscopy with electron probe elemental analysis, x-ray diffraction or infrared spectroscopy.

Apatite deposition can also be associated with scleroderma and other connective tissue diseases, repeated depot corticosteroid injections, high dose vitamin D therapy and injury to the central nervous system. However, in most cases the cause of soft tissue apatide deposition is not known. The acute arthritis or periarthritis can be treated with VSAIDS or colchicine but no agent capable of preventing this potentially destructive type of phase transition is known.

3.2.3 Calcium Oxalate Deposition

Calcium oxalate deposition in joints and other tissue may occur in patients with renal failure on chronic hemodialysis or peritoneal dialysis. Oxalates may deposit in vessels walls and can mimic vasculitis.

3.2.4 Gout

Monosodium urate crystals may deposit in joints and other connective tissue causing gout. Gout is the most common and prototypic of the crystal deposition disease. Monosodium urate crystals are rods or needles up to 15 to 20 micrometers in length and are brightly birefringent with negative elongation when viewed with compensated polarized light.

A variety of lower extremity joints are commonly involved. Chronic or recurrent acute gout can be polyarticular and can mimic rheumatoid arthritis. Crystals are often present in joint fluid even between attacks and may contribute to low-grade inflammation and joint damage. The presence of uric acid crystals in the kidneys can cause renal failure.

Treatment options for gout are also limited with the effective treatment comprising administration of colchicine for acute gout notwithstanding its side effects of nausea, vomiting and diarrhea. A more modem treatment is the use of non-steroidal anti-inflammatory drugs, and in particular the agent indomethicin. Aspirin and aspirin containing products are preferably avoided during acute gout and xanthine oxidase inhibitors such as allopurinol administered to control high levels of uric acid. It should be noted that these are palliative treatments.

Listed below are the differential diagnostic features for some of the crystal-associated arthropathies. (From *Cecil Textbook of Medicine*, Eds. Goldman L. & Bennett J. C., $21^{st}$ Edition (2000), W.B. Saunders Co., Philadelphia)

3.2.5 Renal Calculi (Nephrolithiasis)

Nephrolithiasis is a common disorder defined as the development of stones within the urinary tract. It is a major cause of morbidity in the United States and elsewhere. Approximately 12% of the population of the United States will have a kidney stone at some time in their lives. The economic impact is more than $2 billion dollars per year. Kidney stones are two to three times more common in men than in women and in the U.S. are most common in the southeast.

Formation of kidney stones results from (1) initial formation of crystals (nucleation), (2) reduced effects of normal urinary constituents that inhibit crystal growth and aggregation; (3) the presence of substances promoting crystal growth and aggregation; and (4) the processes that determine crystal attachment to the surface of renal papillary epithelial cells.

As the table below shows, the treatment for many types of renal stones is imperfect and the occurrence of renal calculi continues to cause significant morbidity and high cost to the health care system associated with emergency room visits, etc. Thus there is a need for more effective treatment and, especially, methods of prevention of the formation of renal calculi.

Listed below is a summary of the presently-used treatment options for different types of renal stones. (From *Cecil Textbook of Medicine*, Eds. Goldman L. & Bennett J. C., $21^{st}$ Edition (2000), W.B. Saunders Co., Philadelphia)

| INDICATION | TREATMENT | EXPECTED RESULTS (90% SUCCESSFUL TREATMENT |
| --- | --- | --- |
| All stones | High fluid intake | Unknown |
| Calcium oxalate and brushite (CaOxICaHPO$_4$) stones | | |
| Idiopathic hypercalciuria | 1) Controlled protein Na and Ca diets | Unknown |

| | CRYSTAL SIZE (μM) | CRYSTAL SHAPE | CRYSTAL BIREFRINGENCE AND ELONGATION | OTHER POINTS | X-RAY FINDINGS |
| --- | --- | --- | --- | --- | --- |
| Calciumpyrophosphate | 2–20 | Rods, rhomboids | Weak positive | Elderly and consider associated metabolic diseases | Chondrocalcinosis, bony sclerosis |
| Apatite | 2–25 | Chunks or globules* | Non-birefringement | Clumps stained with alizarin red S | Soft tissue calcification |
| Oxalate | 2–15 | Rods, bipyramids | Positive | Renal failure | Chondrocalcinosis or soft tissue calcification |
| Monosodium urate | 2–20 | Rods, needles | Bright negative | Middle-aged men and elderly women | Cysts and erosions; tophi may calcify |
| Liquid lipid crystals | 2–12 | Maltese crosses | Positive | Unexplained acute arthritis | |
| Cholesterol | 10–80 | Notched rectangles | Positive or negative | May complicate RA and OA | |
| Depot corticosteroids | 4–15 | Irregular or rods | Bright positive or negative | Can cause iatrogenic inflammation | |
| Immunoglobins, other proteins | 3–60 | Rods or irregular | Positive or negative | Cryoglobulinemia | |
| Charcot-Leyden | 10–25 | Spindles | Positive or negative | Eosinophilic synovitis | |

-continued

| INDICATION | TREATMENT | EXPECTED RESULTS (90% SUCCESSFUL TREATMENT |
|---|---|---|
| | 2) Thiazide diuretics and related drugs | 85–90% |
| | 3) Oral phosphate | Unknown |
| | 4) Na cellulose phosphate | Low |
| Hypocitraturia | Potassium citrate | 88% |
| Renal tubular acidosis | Potassium citrate | Unknown |
| Ileostomy or small bowel malabsorption | Potassium citrate | Unknown |
| Hyperoxaluria | | |
| Dietary | Reduced oxalate diet | Unknown |
| Enteric | Low fat diet, calcium supplement, cholestyramine | Unknown |
| Primary | Pyridoxine | Only in a small fraction |
| Hyperuricosuria | Allopurinol | 86% |
| | Potassium citrate | Unknown |
| Uric acid stones | Allopurinol | Unknown |
| | Potassium citrate | 88% |
| Struvite stones | ESWL or percutaneous nephrostolithotomy | 30–40% with stones < 2 cm |
| | Acetohydroxamic acid | Control of stone growth if tolerated |
| Cystine stones/cystinuria | Tiopronin | Unknown |
| | Penicillamine | Unknown |

*Each type of renal stone is listed under indication and the expected success rate per 100 patients is listed under expected results. ESWL is extracorporeal shock wave lithotripsy.

The composition of kidney stones is variable. However, about three-fourths of all stones are composed of calcium oxalate: 35% of stones are pure calcium oxalate (calcium oxalate monohydrate or calcium oxalate dihydrate or both): 40% are calcium oxalate with hydroxyapatite or carbonate apatite; and 1% are calcium oxalate with uric acid. Four percent of all stones are apatite or hydroxyapatite [$Ca_{10}(PO_4)_6(OH)_2$] and 1% are brushite [$CaHPO_4 \cdot 2H_2O$]. The non-calcium-containing crystal stones are struvite (magnesium ammonium phosphate) and comprise 8% of all stones. In addition, eight percent of all stones are composed of uric acid and 2% of cystine. In rare cases stones may be composed of acid ammonium urate or xanthine or insoluble drugs.

3.2.5.1 Diseases of Bone and Bone Mineral Metabolism

Bone is a complex organ system whose functions include support, locomotion encasement of hematopoietic or central nervous system tissue and reservoir for calcium, phosphate and magnesium. The cortices of all bone and the interior of certain bones have a continuous structure termed cortical or lamellar bone. Lamellar bone is characterized by a highly organized extracellular matrix of mineral and parallel bundles of type I collagen. In some pathologic states bone may assume a less organized or so called "woven" architecture.

Bone consists of an organic component called "osteoid" that is able to accumulate a mineral physical-state consisting of amorphous and crystalline states of hydroxy apatite $Ca_5(OH)(PO_4)_3$. Osteoid is primarily (90–95%) composed of bundles of type I collagen which consists of a long triple helix of two $alpha_1$ chains and one $alpha_2$ chain. The collagen of cartilage matrix is type II and is a trimer of three alpha, chains. Elastic tissue consists of type III collagen. The disruption of these various types of collagen produces characteristic disturbances such as Osteogenesis inperfecta (type I collagen) Chondrodysplasia (type II collagen) and Ehlers-Danlar Syndrome or arterial aneurysms (type III collagen).

However, it is the mineralization of bones that is of primary interest here. This process is controlled by several cells characteristic of bone. The osteoblast is a cuboidal bone matrix-synthesizing cell. It lines the surface at which bone formation takes place. The plasma membrane of the osteoblast is highly enriched with a bone specific isoform of the alkaline phosphatase enzyme. This enzyme promotes bone mineralization by catalyzing, in supersaturated extracellular fluid of bone, the hydrolysis of pyrophosphate and other inhibitors of calcium-phosphate crystallization.

The osteoclast is the main bone-resorbing cell. It is a highly mobile multinucleate giant cell with several specialized features for bone. The osteoclast has organells that mediate cell attachment to bone surface (podosomes), a ruffled border at the bone face for ion transport, many enzymes that can function in bone resorption and a high concentration of carbonic anhydrase II which helps acidify the extracellular pocket between the osteoclast ruffled border and the skeletal resorption surface.

The regulation of bone formation and removal is complex and involves both systemic and local regulation. The systemic regulators include parathyroid hormone (PTH), calcitonin and calcitriol. In addition there is a highly complex network of local controls. Only a few of these so called osteoclast-activating factors have been identified. For example interleukin-1 and lymphotoxin/tumor necrosis factor-beta are stimulators of bone resorption that seem to be released locally by some tumors in bone. Parathyroid hormone-related protein (PTH-RP) is a local mediator which may be responsible for the humoral hypercalcemic of malignancy. The activators of bone resorption are poorly understood but insulin-like growth factor type 1 and transforming growth factor-beta are present in osteoblasts and osteocytes and may play a role.

3.2.6 Osteoporosis

Osteoporosis is the most common type of metabolic bone disease and is characterized by a reduction in bone mineral density and bone matrix. Osteoporosis affects 20 million Americans and leads to approximately 1.3 million fractures in the U.S. each year. The disease affects women more than men and it is estimated that women lose about 50% of their trabecular bone and 30% of their cortical bone over the course of their lifetime. By extreme old age, one third of all women and one sixth of all men will have a hip fracture. The annual cost due to osteoporosis has been estimated to be nearly 14 billion dollars in the U.S. alone.

Peak bone density is reached in young adulthood and remains stable for many years, but then declines with age. The rate of bone density loss in women increases several fold after menses cease. During the first 5 to 10 years after menopause, a woman may lose 10% to 15% of her cortical bone and 25%–30% of her trabecular bone mass. Bone density loss rate in men is less, but also increases sharply as age increases.

The loss of bone density caused by osteoporosis results in fractures of the hip, pelvis, wrist, proximal humerus, proximal tibia and vertebral bodies. The disease may be asymptomatic until it results in a fracture, often a vertebral compression fracture, or a fracture of the wrist, hip or pelvis with accompanying pain and disability.

The causes of osteoporosis are many, including decreasing levels of estrogens in women and androgens in men. In addition, many other disorders may lead to osteoporosis, such as hyperprolactinemia, anorexia nervosa, hyperthyroidism, hypercortisolism, and growth hormone deficiency. In addition, many drugs can cause bone loss, such as heparin, ethanol, glucocorticoids and some anti-convulsants.

However, all forms of bone density loss are ultimately the result of the loss of mineralization of bone. At present, few agents capable of stabilizing the solid phase of bone and preventing the phase change that results in loss of biomineralization are known. One such group of agents with this property are the bisphosphonates. These are analogues of pyrophosphate and bind tightly to hydroxyapatite crystals and inhibit osteoclastic bone resorption. However, only one member of this group, alendronate, has been approved by the FDA for prevention of bone loss or treatment of established osteoporosis. An agent that was able to induce biomineralization or inhibit the loss of biomineralization could be an effective treatment for osteoporosis resulting from any cause. In the same way, such an agent could be used to promote bone growth where it is desired, such as at fracture sites and in the regions surrounding bone implants. Such an agent could act as a nucleation site or otherwise act to induce bone formation and/or prevent bone loss.

The methods of the present invention can be used to screen large numbers of agents to determine if they are able to act in this way in the huge variety of circumstances in which this would be desirable.

3.2.7 Diseases Caused by the Extraskeletal Deposition of Calcium and Phosphate

Ectopic mineralization is a consequence of a significant number and variety of disorders. These are illnesses that alter levels of calcium or phosphate or in some other manner cause the abnormal precipitation of amorphous calcium phosphate or hydroxyapatite. In some of these disorders, true bone tissue is formed in abnormal locations. The pathogenesis of this ectopic mineralization is generally due to one of three mechanisms.

First, a supranormal "calcium-phosphate solubility product" in extracellular fluid can cause "metastatic" calcification. Calcium and inorganic phosphate are normally present in serum or extracellular fluid at concentrations that form a "metastable" solution. Their levels are too low for spontaneous precipitation but sufficiently great to cause hydroxyapatite $Ca_{10}(PO_4)_6(OH)_2$ formation once crystal nucleation has begun. This process is controlled by the presence of a variety of inhibitors of mineralization such as inorganic pyrophosphate which helps prevent inappropriate calcification in healthy tissues. However metastatic calcification is a risk if significant hypercalcemia or hyperphosphatemia or both occur for any reason. Direct precipitation of mineral occurs when the critical calcium-phosphate solubility product in extracellular fluid is exceeded. When this parameter (mg/dl×mg/dl) exceeds 75, mineral precipitation will occur. The critical value for renal calcification may be lower and may vary with age. The mineral that is deposited in metastatic calcification may be amorphous calcium phosphate but hydroxyapatite is formed soon after.

The pattern of deposition varies somewhat depending on whether calcium or phosphate is in excess but occurs irrespective of the specific underlying condition or mechanism causing the disturbed mineral homeostasis. In addition there is a predilection for precipitation into certain tissues.

Hypercalcemia is often associated with mineral deposits in the kidney, lungs and fundus of the stomach. In addition, the media of large arteries, elastic tissue of the endocardium (especially the left atrium), conjunctive and peri-articular soft tissues are often affected. In the kidneys, hypercalciuria may cause calcium phosphate casts to form within the tubule lumen or calculi to develop in the calyces or pelvis. Calcium phosphate may precipitate in peritubular tissues. In the lungs, calcification affects the alveolar walls and the pulmonary venous system. Metastatic calcification caused by hypercalcemia is often caused by the Milk Alkali Syndrome, hypervitamosis D, Sarcoidosis, and hyperparathyroidism.

Hyperphosphatemia may occur with idiopathic hyperparathyroidism or pseudohypoparthyroidism and with the massive cell lysis (release of cellular phosphate) that can follow chemotherapy for leukemia. Hyperphosphatemia produces ectopic calcification in locations different from that caused by hypercalcemia. For example, hyperphosphatemia is more likely to result in calcification of periarticular subcutaneous tissues and in certain parts of the CNS such as the cerebral basal ganglion.

A third type of tissue calcification may also occur despite a normal serum calcium-phosphate solubility product. This process is called dystrophic calcification and is precipitated by the release from injured tissue of, as yet unknown, material that has nucleating properties. One example of the phenomenon is the calcification of the lesion of tuberculosis, which will occur with normal levels of calcium and phosphate.

An important type of this "injury induced" or dystrophic calcification commonly occurs in or under the skin in connective tissue disorder and is called "calcinosis." This occurs commonly in Dermatomyositis, Scleroderma and Systemic Lupus Erythematosis. Calcinosis may also occur when tissue is injured by metastasis or trauma. The lesions of calcinosis are small or medium sized hard nodules that can cause muscle atrophy, and contractions, and may produce significant disability.

In addition to diseases in which calcium phosphate is deposited in tissue because of a high solubility product or because of release of materials that have nucleating properties, it is also possible for "true" bone to form ectopicly. The bone formed in these diseases is lamellar, actively remodeled by osteoblasts and osteoclasts, and like true bone, has Haversian systems and sometimes contains marrow. In this case, the injured or diseased tissue contains all the necessary precursor cells and inductive signals to form bone. This phenomenon may occur following an injury or trauma or may occur as a separate heritable entity called Fibrodysplasia Ossificans Progressiva.

3.2.8 Mineralization to Form Dental Calculus

Opinions in the dental profession vary as to the relative importance of dental calculus versus plaque as the major cause of periodontal disease. Dental plaque is the accumulation of bacteria and organic matter on teeth. Dental calculus is the formation of calcium phosphate crystals around and in this organic matter. Therefore, formation of the hard deposits of dental calculus involves the mineralization of the plaque deposits. (See Mandel et al. 1986, *J. Clin. Periodontal* 13: 249–257; Saomi et al. 1974, *J. Periodontal* 1:139–145).

Dental calculus is a distinct oral detriment because it is especially difficult to remove with dental floss and serves as a localized physical irritant to the gingival tissue. Furthermore, dental calculus contains endotoxins and other microbial constituents which are etiological factors in the initiation of gingivitis. Perhaps of greatest importance is that dental calculus has greater porosity as compared to the normal tooth surface and this allows the bacterial accumulation that enables dental plaque to occur at a faster rate. (See Beiswanger et al., 1989, *J. Clin. Dent.* 1:55–58).

Experimental studies of mineralization in developing human-dental calculus suggest a close parallelism to the mineralization process of other calcified tissues, such as bone. (See Zander et al., 1960 *Mineralization of Dental Calculus Proceeding Society for Experimental Biology and Medicine* 103:257–260). However, the calcification of hydroxyapatite in dental calculus formation occurs in an organic matrix consisting of microorganisms and intermicrobial substances.

Studies have found agents with some degree of anti-calculus effect. (See Suomi et al.1974, *J. Periodontal* 1:139–145). However, no generally effective means to control the formation of dental calculus is known.

3.2.9 Gallstone Formation

Gallstones are concretions that form in the biliary tree, mostly in the gallbladder when conditions favor the precipitation, as solid crystals, of certain biliary solutes such as cholesterol and calcium that are normally held in solution. These crystals may grow and aggregate within the mucus layer lining the gall bladder.

The prevalence of gallstones in the U.S. population is 10–15% and gallstone disease is responsible for about 10,000 deaths annually. Each year in the U.S. over 500,000 gallbladders are removed at a cost of over 6 billion U.S. dollars.

Gallstones are formed when bile becomes supersaturated with cholesterol or calcium. The conditions must allow the solute to nucleate from solution and precipitate as solid crystals of cholesterol or bilirubin. The third step in the process occurs when the crystals aggregate and fuse to form stones. This aggregation occurs in a mucus gel along the wall of the gallbladder. In addition, gallstone formation may be associated with impaired gallbladder motility resulting in impaired contractile response of the gallbladder muscle to cholecystokinin. This is thought to be secondary to cholesterol accumulation in the gallbladder muscle itself.

Cholesterol gallstones are yellow-brown and range in size from a few millimeters to 2–3 cm. More than 50%, and often over 90%, of their dry weight consists of crystalline cholesterol monohydrate. Small but variable amounts of other components such as mucin glycoproteins and calcium bilirubinate may also be present. Cholesterol gallstones form when the amount of cholesterol secreted into bile exceed the amount that can be held in stable micellar solution by the concentrations of bile salts and lecithin present. The cholesterol saturation index indicates the degree of cholesterol saturation of the bile. An index value greater than one indicates supersaturation. When bile is unsaturated, newly secreted vesicles containing cholesterol and lecithin are dissolved completely by bile salts as bile is concentrated in the gallbladder. However, if the bile is supersaturated, vesicles fail to dissolve completely and instead fuse to form large, cholesterol-rich multilamellar liquid crystals from which excess cholesterol may precipitate as plate-like cholesterol monohydrate crystals.

Biliary cholesterol supersaturation can be caused by a primary increase in biliary secretion of cholesterol or by a deficiency of bile salts.

Estrogen causes an increase in the rate of biliary cholesterol secretion into bile. This may account for the two-fold increase risk of cholesterol gallstones in women during their childbearing years.

Obesity is also associated with an increased biliary cholesterol secretion. In addition some hypocholesterolemic drugs such as the fibric acid derivatives clofibrate and gemfibrizol directly stimulate secretion of cholesterol into bile and are associated with increased risk of cholesterol gallstones.

Approximately 20% of U.S. gallstones are pigment gallstones. These stones are composed of calcium salts of organic and inorganic anions, especially bilirubin. Ionized calcium is present in bile at concentrations similar to those of plasma. Unconjugated bilirubin has a low solubility product with calcium and its presence in bile even in small amounts favors precipitation of calcium bilirubinate.

Two subtypes of pigment gallstones have different compositions, different pathogenesis and different risk factors. Black pigment gallstones are hard, dense, brittle concretions composed of calcium bilirubinate along with inorganic calcium salts of carbonate and phosphate.

Brown pigment gallstones have a soft clay-like consistency. They contain calcium bilirubinate plus a substantial proportion of calcium soaps of fatty acids. Brown pigment stones occur in chronically infected bile in areas of stasis, where bacterial cleavage of phospholipid and conjugated bilirubin releases unconjugated bilirubins and fatty acids.

Bile supersaturation is only one of a variety of abnormalities which contribute to the formation of both cholesterol and pigment gallstones. Precipitation of crystals from supersaturated bile requires the formation of an initial solid nidus (nucleation) with subsequent deposition of solute on the surface leading to crystal growth. Some individuals have very slow nucleation and do not develop gallstones despite secreting supersaturated bile. Nucleation and growth of cholesterol crystals is much more rapid in bile of gallstone patients than in gallstone-free controls for equal degrees of cholesterol supersaturation. The nucleation and growth of cholesterol crystals may be accelerated or retarded by the presence of certain proteins in bile. Nascent cholesterol crystals precipitating from vesicles or mixed micelles are trapped in a mucin gel lining of the gallbladder. Over time these crystals fuse to form macroscopic stones. Mucus secretion is stimulated by prostaglandins and in animal models the prevention of excessive mucin secretion by cycloxygenase inhibitors can prevent cholesterol gallstone formation. Thus the formation of gallstones is a major medical problem associated with significant morbidity and mortality and expense.

3.2.10 Sickle Cell Disease

Sickle cell disease is an inherited disorder caused by the abnormal properties of red blood cells containing a form of mutant sickle cell hemoglobin (HbS). Normal hemoglobin is a complex protein formed from two alpha and two beta globin polypeptide chains. In sickle cell disease the affected individual has inherited a mutant gene for beta-globin. This mutation is the substitution of a T for an A in the sixth codon of the beta-globin gene. This single nucleotide substitution causes a substitution of the amino acid Glu for Val on the sixth position of the polypeptide chain that forms beta-globin. This seemingly minor change in amino acid composition of the globin protein causes a profound change in the solubility of deoxygenated hemoglobin containing either one or two such abnormal beta-globin molecules. When sickle cell hemoglobin is deoxygenated the abnormal solu bility of the mutant hemoglobin allows a dramatic and pathological phase change to occur in which the HbS polymerizes and causes impaired deformability and "sickling" of polymer containing erythrocytes. This rigid deformation of the red blood cells, in turn, causes occlusion of the microvasculature.

The clinical features that result from this "sickling" process are numerous and varied and depend on whether the gene for the abnormal hemoglobin is inherited from one or both parents. In the former case the condition is called sickle cell trait and is largely asymptomatic. However, when the mutant gene is inherited from both parents then sickle cell disease results and this is associated with chronic anemia and recurrent pain and the periodic occurrence of, possibly life threatening "sickle cell crisis". Such an acute episode of sickle cell disease may be the first symptom of the disease and may be precipitated by cold, dehydration, infection, stress, menses or alcohol consumption or the cause may be indeterminate. The resulting pain may affect any area of the body but most commonly the back, chest, extremities and abdomen are involved. In addition to pain these episodes are often associated with fever, swelling, tenderness, tachypnia, hypertension, nausea and vomiting and may last from hours to days.

Sickle disease can cause serious organ damage due to the reduction of blood flow in small vessels. For example, the growth and development of a child with sickle disease may be retarded and specific damage may occur to the CNS, lungs, kidney, eyes, heart and skin. In addition, a common and extremely serious condition called osteonecrosis may occur because of the reduction of blood flow to the bones, resulting in painful bone infarctions.

The phase change responsible for sickle cell disease is the result of the decrease in solubility of deoxy-HbS as compared to the solubility of normal hemoglobin, e.g. from 34 g/dL to 17 g/dL. Thus deoxygenation in the tissues causes rapid supersaturation with aggregation and polymerization of the abnormal hemoglobin and resulting large scale deformation of red blood cells containing such hemoglobin. This deformation causes vaso-occlusion and the resulting decrease in blood supply causes the diverse symptoms of the disease.

The progression from nuclear aggregation to polymer formation has a delay time inversely related to the $30^{th}$ power of the deoxy-HbS concentration. The resulting polymer fibers provide additional nuclei for further polymer formation. However, the delay times usually exceed capillary transit times and so cells do not accumulate significant amounts of polymer until they are in a large vein where they cannot elicit vasoocclusion. Unfortunately local vascular perturbations may cause unusual delay in the transit time and allow sickling to take place in the capillary, causing a potentially disastrous decrease in blood supply to the organ.

Patients with sickle cell disease can be treated with blood transfusions to reduce the concentration of abnormal hemoglobin in their circulation. However this is primarily an emergency procedure and has many disadvantages, such as transmission of infectious agents and high cost.

No simple agent is known that would inhibit the phase transition that allows the abnormal polymerization of HbS when deoxygenated. The methods of this invention would allow the high-throughput screening of agents to determine if they can prevent or diminish this pathological phase transition and the resulting disease symptoms.

3.2.11 Cataracts

Cataracts are caused by the opacification of the crystalline lens of the eye. They are the leading cause of blindness in the world and the leading cause of visual loss in Americans older than age 40. The prevalence of cataract in the United States has been estimated at 50% for persons older than age 75. Genetic predisposition to senile cataract has been hypothesized but not proven. However, it is known that exposure to ultraviolet light, trauma to the eye, Wilson's disease or systemic corticosteroid use may all cause cataract formation.

The formation of cataracts is the result of a phase change in the substance of the lens causing progressive yellowing and opacification of the lens nucleus (nuclear sclerosis). The normal protein matrix of the lens may cross link and precipitate over the course of time causing loss of transparency to visual light.

Although cataracts may be treated surgically by removal of the opacified lens, no agent capable of preventing the phase transition responsible for this tissue change is known. The methods of this invention may be used to screen large number of agents for their ability to slow or prevent this phase transition.

3.2.12 The Amyloid Diseases

Amyloidosis is not a single clinical entity but group of diverse diseases characterized by protein deposition. They are similar in that the protein deposition occurs extra cellularly and these deposits stain esinophilic with standard tissue histologic stains, bind Congo red dye and emit an apple-green birefringence when examined under polarized light microscopy. In addition, these protein deposits exhibit metachromasia with crystal violet and have an array of 75–100 A non-brushing fibrnls by electron microscopy and a twisted beta-pleated sheet antiparallel configuration by x-ray crystallography. However, the various amyloid diseases differ in the biochemical nature of the proteinaceous deposits, the "etiology" of the associated diseases (neoplastic, inflammatory degenerative, hereditary), the tropism of protein deposition and the spectrum of disease manifestations.

All the monomeric amyloidgenic proteins have a beta-pleated sheet conformation in solution and many form insoluble beta pleated sheet fibrils in vitro. It is the formation of this periodic beta-pleated sheet that accounts for the known properties of tissue amyloid deposits such as binding to Congo red, resistance to proteolysis and insolubility in physiologic solution. The formation of beta-pleated sheets in vivo is an extremely complex process involving crucial ion concentrations and hydrogen bonding between many similar monomeric polypeptide chains at high focal concentrations as well as molecular interactions with extra-cellular matrix components. In addition, most amyloid deposits contain P component, an acute-phase circulating serum protein.

No clinical classification of the amyloid diseases is entirely satisfactory. One method is to consider three major systemic forms—AA, AL and ATTR; two major localized forms $A\beta_2$ and $A\beta$ and several miscellaneous forms as shown in the following table. (From *Cecil Textbook of Medicine*, Eds. Goldman L. & Bennett J. C., $21^{st}$ Edition (2000), W.B. Saunders Co., Philadelphia)

| | NOMENCLATURE AND CLASSIFICATION OF THE AMYLOIDOSES, 1990 | | |
|---|---|---|---|
| | AMYLOID PROTEIN | CLINICAL STATE(S) | MAJOR ORGAN/TISSUE INVOLVEMENT* |
| Major systemic amyloidoses | 1 AA | 1. Chronic inflammatory conditions | K, L, S, GI, Sc |
| | | a. Infectious. tuberculosis, osteomyelitis, etc. | H, unusual |
| | | b. Non-infectious. juvenile rheumatoid arthritis, ankylosing spondylitis, Chrohn's disease, etc. | N, rare |
| | | 2. Familial Mediterranean Fever | |
| | 2 AL | Plasma cell dyscrasia | H, L, S, T |
| | | 10% multiple myeloma/macroglobulemia | N, GI, Sc |
| | | 90% idiopathic; "primary" | |
| | 3. ATTR | Various familial polneuropathies and cardiomyopathies | N, H, K, E, GI, Sc B, Sy, Ts |
| Major localized amyloidoses | 4. A$\beta_3$M | Chronic dialysis usually longer than 8 yr | |
| | 5. A$\beta$ | 1. Alzheimer's disease | |
| | | 2. Down syndrome | |
| | | 3. Hereditary cerebral hemorrhage, Dutch | C, CV |
| | | 4. Non-traumatic cerebral hemorrhage of the elderly | |
| Miscellaneous amyloidoses | 6. A Apo AI | Familial polyneuropathy, Iowa | N, K |
| | 7 A Gel | Familial amyloidosis, Finnish | CN, E, skin |
| | 8. A Cys | Hereditary cerebral hemorrhage, Icelandic | C, CV |
| | 9. A Scr | Creutzfeldt-Jakob disease | C |
| | 10. A Cal | Medullary carcinoma of the thyroid | Th |
| | 11. AANF | Atrial amyloid | H |
| | 12. AIAPP | Diabetes mellitus, insulinomas | P |

*B = bone; C = cerebrum; CN = cranial nerves; CV = cerebral vessels; E = eye; GI = gastrointestinal; H = heart; K = kidney; L = liver; N = nerve; P = pancreas; S = spleen; Sc = subcutaneous tissue; T = tongue; Th = thyroid; Ts = tenosynovium; Sy = synovium.

3.2.12.1 Primary (AL) Amyloidosis

AL amyloid was the first amyloid protein defined biochemically and shown to be identical to the variable region of immunoglobulin light chain (Bence Jones protein). AL is the most common of the amyloidoses in the U.S. and is associated with plasma cell myeloma (20%) or plasma cell dyscrasias (80%). The symptoms vary depending on organ involvement but often include carpal tunnel syndrome, peripheral neuropathy with paresthesias of the fingers and toes and sympathetic dysfunction manifested by orthostatic hypotension and congestive heart failure.

3.2.12.1.1 Secondary (AA) Amyloidosis

AA amyloidosis was the $2^{nd}$ systemic type of amyloidosis shown to be due to protein deposition. The precursor protein is a serum component called serum amyloid A that is synthesized in the liver. The production of this protein may increase 100–200 fold following an inflammatory stimulus. In addition, certain monocyte/macrophage cytokines such as interleukin 1 (IL-1), tumor necrosis factor and IL-6 may up-regulate hepatic gene expression of this protein. The organs most commonly involved include liver, spleen and kidney with heart and nerve involvement less frequent then seen in primary amyloidosis.

The infectious diseases which often trigger this form of amyloidosis include osteomyelitis, tuberculosis and bronchiectasis. In addition, non-infectious inflammatory states including Rheumatoid Arthritis, Juvenile Rheumatoid Arthritis, Ankylosing Spondylitis, Crohn's Disease and Familial Mediterranean Fever, can act as the triggers.

3.2.12.2 Familiar (ATTR) Amyloidosis

ATTR amyloidosis is caused by the presence of an abnormal plasma pre-albumin protein that normally functions to transport thyroxine and retinol-binding protein and was subsequently termed transthyretin. Since the discovery of this form of amyloid many different clinical manifestations resulting from the more than 50 mutations in the gene for transthyretin have been identified. The major organ systems involved include the heart, bowel and kidney.

3.2.12.3 Dialysis-Related ($\beta_2$ Microglobulin) Amyloidosis (A$\beta_2$M)

This form of amyloidosis occurs in patients undergoing maintenance hemodialysis or peritoneal dialysis for longer than 8 years. $\beta_2$-Microglobin is the non-covalently associated chain of class I major histocompatibility complex molecules and is present on virtually all human nucleated cells. Catabolism of this small protein depends on normal kidney filtration and excretion. In dialysis patients and those with end-stage renal disease plasma levels of $\beta_2$-Microglobulin are elevated. The symptoms result from the deposition of this amyloid protein in periarticular, joint, bone and carpal tunnel tissue.

3.2.12.4 $\beta$-Protein Amyloidosis (Alzheimer's Disease)

Alzheimer's disease is the most common cause of dementia in elderly patients and afflicts between 5 and 10% of the population older than 65 years. Neuropathologic studies of the brain of patients with Alzheimer's disease show neurofibrillary tangles and neuritic plaques in the amygdala, hippocampus and frontal, temporal and parietal lobes. Also seen in patients with Alzheimer's disease are a cellular thickening of the small and medium-sized arteries of the leptomeninges and cerebral cortex. The amorphous material in the walls of meningeal vessels and the central region of neuritic plaques has the characteristic staining property for amyloid. The chemical nature of these amyloid deposits has been identified as a novel 42-amino acid protein ($\beta$-protein) that is generated by proteolysis of a much larger transmembrane glycoprotein termed "$\beta$ amyloid precursor protein". In some forms of familial Alzheimer's disease point mutations have resulted in single-amino acid substitutions in this precursor protein.

3.2.13 Prion Diseases

Several human diseases have been attributed to a type of physical-state transition induced by a unique infectious protein referred to as the "prion". The prototypical human illness is Creutzfeldt-Jakob Disease (CJD), but several others are known including Kuru, Gerstmann-Straussler-Scheihker Syndrome and Familiar Fatal Insomnia. Many of these illnesses were formerly thought to be caused by slow acting viruses.

However, it is now known that the prion protein (PRP) exists as a membrane-bound sialoglycoprotein that is a normal cellular constituent distributed primarily in the brain. Neurons contain high concentrations of cellular PrP (PrP$^c$) and the protein appears to be developmentally regulated.

Prion diseases are due to an abnormal isoform of PrP$^c$ referred to as PrP$^{sc}$. This is produced by a post translational change in the conformation of PrP$^c$ which normally exists as an alpha-helical structure. The normal protein can be induced to change conformation to PrP$^{sc}$, which consists of β-pleated sheets. The abnormal protein configuration resists proteolytic digestion and spontaneously aggregates to produce rod like or fibrillary particles, called prion rods. These structures can be isolated from the brains of animals and humans with this class of illness.

The clinical manifestations of CJD and other prion disease are protean and frequently incorrectly diagnosed initially. The symptoms begin with altered sleep patterns and appetite, weight loss and complaints of impaired memory and concentration. The diseases usually progress rapidly to global dementia, often with myoclonus and seizures. Death typically occurs within 1 year of the onset of symptoms.

Clearly, there is a tremendous need for drugs or other therapies (e.g., nutritional regulation) to treat or prevent the diseases and symptoms enumerated above. But given the enormous variety of disorders due to physical-state changes in animals, it has been extremely tedious to perform the huge number of experiments to determine the conditions, compounds, or compositions that will prevent, inhibit, or reverse these undesirable physical-state changes or promote or induce desirable physical-state changes. And because many factors influence crystallization, precipitation, deposition, and other physical-state changes of inorganic and organic substances, testing to find conditions, compounds, or compositions that can inhibit or reverse such processes or induce desirable physical state changes is an extremely tedious process.

At present, industry does not have the time or resources to test hundreds of thousands of combinations to find the right conditions, compounds, or compositions adverse to undesired physical-state changes. To remedy these deficiencies, methods for rapid screening of conditions, compounds, or compositions of thousands to hundreds of thousands of samples per day, cost effectively, are needed. The invention disclosed herein addresses the issues discussed above.

4. SUMMARY OF THE INVENTION

In one embodiment, the invention provides practical and cost-effective methods to rapidly produce and screen hundreds, thousands, to hundreds of thousands of samples per day. These methods provide an extremely powerful tool for the rapid and systematic analysis, optimization, selection, or discovery of conditions, compounds, or compositions that prevent, inhibit, induce, modify, or reverse physical-state transition.

In a further embodiment, the invention relates to optimization, selection, or discovery of compounds or compositions that prevent or inhibit crystallization, precipitation, formation, or deposition of inorganic and organic substances, or that promote dissolution, destruction, modification, or breakup of inorganic and organic solids, particularly disease-causing substances. The invention further encompasses the use of such compounds or compositions to treat (e.g., reverse) or prevent the disease itself, the cause of the disease, or the symptoms of the disease.

The invention further encompasses a method for the discovery of physiological conditions (e.g., pH, salt concentration, protein concentration, hormone concentration, etc.) that inhibit or prevent crystallization, precipitation, formation, or deposition of inorganic or organic substances or that promote dissolution or breakup of inorganic and organic solids, particularly disease-causing substances. Once such conditions are identified, the invention further contemplates the use of drugs or other therapies to achieve these physiological conditions, and thereby prevent or treat the disease itself, the cause of the disease, slow or modify progression of the disease, or the symptoms of the disease.

The invention also encompasses methods to discover compounds, compositions, or physiological conditions that prevent or inhibit a change in physical state of a solid substance, for example, prevention or inhibition of a polymorphic shift of a benign solid to a disease-causing substance or mineralization of a plaque to form a disease-causing substance.

The invention further encompasses methods to discover compounds, compositions, or physiological conditions that prevent or inhibit unfavorable biocrystallization or bioprecipitation of pharmaceuticals, such as physiologically low-solubility pharmaceuticals or pharmaceuticals that complex with tissue or other bodily substances.

In another embodiment, the invention encompasses methods to discover compounds, compositions, or physiological conditions that promote, potentiate, or induce a change in physical state. For example, promotion of bone growth or mineralization.

In one embodiment, the invention comprises arrays for screening to identify conditions, compounds, or compositions that inhibit, prevent, induce, modify, or reverse transitions of physical state comprising at least 24 samples, each sample comprising a medium, wherein one or more of the samples comprises a disease-causing substance.

In another embodiment, the invention concerns a method of preparing an array of at least 24 samples for screening to identify conditions, compounds, or compositions that inhibit, prevent, induce, modify, or reverse transitions of physical state comprising:

(a) adding a medium to each of the samples; and
(b) adding a disease-causing substance to at least one of the samples.

In still another embodiment, the invention relates to a method of screening an array of at least 24 samples to identify conditions, compounds, or compositions that inhibit, prevent, induce, modify, or reverse transitions of physical state comprising:

(a) preparing an array of at least 24 samples each sample comprising a medium and a disease-causing substance;
(b) processing one or more of the samples to induce or reverse the transition of physical-state in the disease causing substance; and
(c) analyzing the processed samples to detect the induction or reversal of the transition in physical state.

In yet another embodiment, the invention concerns a method to discover conditions, compounds, or compositions that prevent or inhibit crystallization, precipitation, or deposition of a disease-causing substance, comprising:

(a) preparing an array comprising at least 24 samples each sample comprising a medium and one or more components to induce a disease-causing substance;

(b) processing one or more of the samples to induce crystallization, precipitation, or deposition of the disease-causing substance;

(c) screening the array by analyzing the processed samples to detect the absence of crystallization, precipitation, or deposition of the disease-causing substance; and (d) selecting the samples wherein crystallization, precipitation, or deposition of the disease-causing substance did not occur to identify the conditions, compounds, or compositions.

In another embodiment, the invention comprises a method to discover conditions, compounds or compositions that promote dissolution, destruction, or breakup of a disease-causing substance, comprising:

(a) preparing an array comprising at least 24 samples each sample comprising a medium and the disease-causing substance;

(b) processing one or more of the samples to induce the dissolution, destruction, or breakup of the disease-causing substance;

(c) screening the array by analyzing the processed samples to detect the dissolution, destruction, or breakup of the disease-causing substance; and (d) selecting the samples wherein the dissolution, destruction, or breakup of the disease-causing substance occurred to identify the conditions, compounds, or compositions.

These and other features, aspects, and advantages of the invention will become better understood with reference to the following detailed description, examples, and appended claims.

5. DETAILED DESCRIPTION OF THE INVENTION

As an alternate approach to traditional methods for discovering pharmaceuticals, applicants have developed practical and cost-effective methods to rapidly produce and screen hundreds, thousands, to hundreds of thousands of samples per day. These methods are useful to optimize, select, and discover compounds, compositions, or conditions that prevent or reverse undesirable changes in physical state or that induce desirable changes in physical state. For example, these methods are useful to optimize, select, and discover compounds, compositions, or conditions that prevent or inhibit crystallization, precipitation, formation, or deposition of inorganic and organic substances, or that promote dissolution, destruction, or breakup of inorganic and organic solids, particularly disease-causing substances. Such conditions, compounds, or compositions can be exploited to treat (e.g., reverse) or prevent the disease itself, the cause of the disease, or the symptoms of the disease. Such conditions, compounds, or compositions can also be exploited promote desirable physical-state transitions, such as bone mineralization.

In the preferred embodiment, the samples are prepared in a grid or array (i.e., an ordered set of components) such as a 25, 48 or 96 well plate. Each sample in the array comprises a medium and at least one of the samples comprises a disease-causing substance, in solid, liquid, or dissolved form.

The array or selected samples therein can be subjected to processing parameters. Examples of processing parameters that can be varied include temperature, temperature gradient, time, the identity or the amount of the disease-causing substance, the identity or the amount of the medium, or the identity or the amount of the components.

After processing, each sample in the processed array can be screened to determine whether a change in physical state occurred, particularly a change in the physical state of a disease-causing substance. The presence or absence of a solid can be assessed by turbidity, using a device such as a spectrophotometer. But a simple visual analysis can also be conducted including photographic analysis. Crystal forms, different polymorphs, and other amorphous solids are then determined. The samples containing a solid can then be screened to analyze the solid's properties, such as structural, physical, pharmacological, or chemical properties. In a preferred embodiment, the samples are screened to define the conditions, compounds, or compositions, that prevent or inhibit crystallization, precipitation, formation, or deposition of inorganic and organic substances, or that promote dissolution, destruction, or breakup of inorganic and organic solids, particularly disease-causing substances. Systems employing these methods have been designed to rapidly, systematically, and inexpensively screen such samples. The methods and systems are widely applicable.

5.1 Helpful Definitions 5.1.1 Array

As used herein, the term "array" means a plurality of samples, preferably, at least 24 samples. Each sample comprises a medium, and at least one of the samples comprises a disease-causing substance. Preferably, each sample comprises the disease-causing substance, with the exception of negative controls. Each sample can have different components or concentrations of components. The samples are associated under a common experiment. An array can comprise 24, 36, 48, 96, or more samples, preferably 1000 or more samples, more preferably, 10,000 or more samples. An array is typically comprised of one or more groups of samples also known as sub-arrays. For example, a sub-array can be a 96-tube plate of sample tubes or a 96-well plate of sample wells in an array comprising 100 plates.

Arrays can be assembled by preparing a plurality of samples using standard addition and mixing techniques. If desired, each sample, selected samples, or selected sub-arrays can be subjected to the same or different processing parameters. For example, an array can be processed to prevent or inhibit crystallization, precipitation, formation, or deposition of the disease-causing substance, or to promote dissolution, destruction, or breakup of the disease-causing substance. Arrays can be processed by a variety of methods readily ascertainable by one skilled in the art according to the objective of the experiment. For example, the array can be stored at a particular temperature, such as room temperature. The samples can be subjected to a temperature gradient, such as cooling the sample. Or the pH can be adjusted by adding acidic or basic components. The array can also be subjected to standard methods well known in the art to prevent or inhibit crystallization, precipitation, formation, or deposition of the disease-causing substance, or that promote dissolution, destruction, or breakup of the disease-causing substance, for example, but not limited to, ultrasound, shock-waves, or laser energy.

5.1.2 Disease-causing substance

As used herein, the term "disease-causing substance" means any solid, semisolid, paste, gel, plaque, or liquid in dissolved or undissolved form, that can crystallize, precipitate, or otherwise accumulate or deposit in solid form in an animal body, thereby causing or aggravating a disease process. Examples of disease-causing substances include, but are not limited to, calcium salts and compositions thereof, such as calcium phosphate, calcium carbonate, calcium pyrophosphate, brushite, apatite, hydroxyapatite, calcium oxalate, kidney stones, and bone tissue; magnesium salts and compositions thereof, such as magnesium ammonium phosphate; uric acid and salts thereof; cholesterol and cholesterol compositions, such as cholesterol gall stones; bilirubin, salts thereof, and compositions thereof, such as pigment gall stones; or hydrates and mixtures thereof; tooth plaque; dental calculus; and protein precipitates, such as amyloid protein deposits.

Disease-causing substances can form in vivo—and thus can be isolated from an animal, plant, tissue, or cell culture—or they can be prepared in a laboratory setting to mimic one or more physical, chemical, or structural properties of those formed in vivo. Disease-causing substances derived from animals and plants are often complex mixtures, thus, those prepared in a laboratory setting will usually only approximate those formed in vivo.

5.1.3 Medium

As used herein the term "medium" is the solution in which the inhibition or promotion of various phase transitions or changes of physical state are tested. Preferably, a medium will be chosen to mimic the physiologic conditions under which such changes occur in vivo. Thus, the precise composition of the medium will depend on which phase transition or change in physical state is being investigated. Thus, for example the formation of renal calculi will be investigated in solutions that are similar to the composition of urine in various parts of the kidney and bladder. The formation of gallstones will be investigated in a medium that reproduces the conditions that occur in normal bile and the bile that occurs in various disease states such as hypercholesterolemia and hypocalcemia. Likewise, the changes in physical state that result in tissue calcification may be investigated in mediums that are similar in composition to blood plasma, or to the fluid in the extracellular or intracellular spaces, in joints spaces or in saliva in normal and various disease states.

One of skill in the art will be aware that the exact composition of the medium employed will depend on the nature of the phase transition or change in physical state being investigated, but will be primarily water based. These solutions may vary in pH, electrolyte concentration, protein concentration, and the presence or absence of various organic and inorganic compounds such as cholesterol, bile salts, sodium, potassium, calcium ions or mucins, polysaccarides or proteins. These media may be obtained from natural sources such as blood plasma, urine, bile and joint space fluid or can be prepared by means well known to one of ordinary skill in the art.

5.1.4 Sample

As used herein, the term "sample" means at least a medium isolated at a particular location or site, preferably, further comprising a disease-causing substance. A sample can comprise multiple disease-causing substances. In addition, a sample can comprise one or more components. Preferably, the amount of the disease-causing substance is less than about 100 milligrams, more preferably, less than about 1 milligram, even more preferably, less than about 100 micrograms. Preferably, the sample has a total volume of about 5 µl to about 500 µl, more preferably, about 10 µl to about 200 µl.

A sample can be contained in any container or holder, or present on any material or surface, or absorbed or adsorbed in any material or surface. The only requirement is that the samples are isolated from one another, that is, located at separate sites. In one embodiment, samples are contained in sample wells in standard sample plates, for instance, in 24, 36, 48, or 96 well plates (or filter plates) of volume 250 µl commercially available, for example, from Millipore, Bedford, Mass.

In another embodiment, the samples can be contained in glass sample tubes, for example, individual glass tubes in a metal support plate. The tube is equipped with a plunger seal having a filter frit on the plunger top. The medium and other substances or components are distributed in the tubes, and the tubes sealed. The sealing is accomplished by capping with a plug-type cap. Preferably, both the plunger and cap are injection molded from thermoplastics, ideally chemically resistant thermoplastics such as PFA (although polyethylene and polypropylene are normally sufficient). This tube design allows for both removal of the medium from tube as well as harvesting any solids therein. Specifically, the plunger cap is pierced with a standard syringe needle and the medium is aspirated through the syringe tip by well-known methods. By having the frit barrier between the medium and the syringe tip, any solid can be separated from the medium. Once the medium is removed, the plunger is then forced up the tube, effectively scraping any solid substance present on the walls, thereby collecting the solid substance on the frit. The plunger is fully extended at least to a level where the frit, and any collected solid substance, are fully exposed above the tube. This allows the frit to be inserted into the under-side of a custom etched glass analysis plate. This analysis plate has 96 through-holes etched corresponding to the 96 individual frits. The top-side of the analysis plate has an optically clear glass plate bonded onto it to both seal the plate as well as provide a window for analysis. The analysis plate assembly, which contains the plate itself plus the added frits with the solid substance, can be stored at room temperature, under an inert atmosphere if desired. The individual sample tube components are readily constructed from HPLC auto-sampler tube designs, for example, those of Waters Corp (Milford, Mass.). The automation mechanisms for capping, sealing, and sample tube manipulation are readily available to those skilled in the art of industrial automation.

According to one embodiment of the invention, the amounts or the identity of the medium, the components, or the disease-causing substance can vary between samples. For example, within an individual array or sub-array, one or more of the samples can differ from one or more of the other samples with respect to:

(i) the identity or the amount of the disease-causing substance;
(ii) the identity or the amount of the medium; or
(iii) the identity or the amount of at least one of the components.

such amounts and identities will differ between samples when they are intentionally varied to induce a measurable change in the sample's properties. Thus, according to the invention, minor variations between samples, such as those introduced by slight weighing and measuring errors, are not considered intentionally varied.

5.1.5 Component

As used herein, the term "component" means any substance that is combined, mixed, or processed in the medium comprising a sample. A single component can exist in one or more physical states. Examples of suitable components include, but are not limited to, compounds and compositions that prevent or inhibit precipitation, formation, crystallization, or nucleation of inorganic and organic substances, such as pyrophosphate and citric acid salts; compositions and compounds that promote dissolution, etching, destruction, or breakup of inorganic and organic solids; nucleation promoters (also known as crystallizing aids), such as seed crystals or surfactants, and combinations thereof; compositions or compounds that affect crystal habit; nutrients, such as vitamins and minerals; small molecules (i.e., molecules having a molecular weight of less than about 1000 g/mol), such as pharmaceuticals (e.g., ursodeoxycholic acid; diuretic agents, thiazides, and allopurinol); large molecules (i.e., molecules having a molecular weight of greater than about 1000 g/mol), such as oligonucleotides, proteins (e.g., proteins isolated from the body, such as amyloid proteins or corneal proteins like crystallin), and peptides; hormones; steroids; matrix and connective tissue, such as cartilage and collagen; biological-membrane extracts; chelating agents, such as EDTA; anti-dental-calculus agents; excipients; organic solvents; water; salts; acids; bases; gases; and stabilizers, such as antioxidants.

The term "component" also encompasses disease-causing solids, which, as discussed herein, can be added to samples according to certain embodiments of the invention.

The term "component" further encompasses the ingredient or one of the ingredients in the sample medium—in dissolved or undissolved form—that can induce or result in crystallization, precipitation, formation, or deposition of a disease-causing substance within the sample.

5.1.6 Processing Parameters

As used herein, the term "processing parameters" means the physical or chemical conditions under which a sample is subjected and the time during which the sample is subjected to such conditions. The period of incubation is also a processing parameter and means the time that a sample is given to undergo a change in physical state. For example, an array of samples can be incubated for 3 days at normal human-body temperature, then analyzed for a change in physical state. Processing parameters include, but are not limited to, adjustments in time of incubation, temperature, pressure, pH, chemical environment, subjecting the samples to a nucleation event, ultrasound, shock waves, laser energy, or mechanical stimulation, or any other conditions that can induce a change in physical state. Processing also includes adjusting the concentration of components, adding various additional components, or adjusting the composition or amount of the medium during incubation. Processing also includes parameters such as adjusting the oxygen tension or oxygen vapor pressure. A sample can be processed to prevent or inhibit crystallization, precipitation, formation, or deposition of inorganic and organic substances, or to promote dissolution, destruction or breakup of existing inorganic and organic solids, particularly disease-causing substances.

Sub-arrays or even individual samples within an array can be subjected to processing parameters that are different from the processing parameters to which other sub-arrays or samples, within the same array, are subjected. Processing parameters will differ between sub-arrays or samples when they are intentionally varied to induce a measurable change in the sample's properties. Thus, according to the invention, minor variations, such as those introduced by slight adjustment errors, are not considered intentionally varied.

5.1.7 Property

As used herein, the term "property" means a structural, physical, pharmacological, or chemical characteristic of a sample, preferably, a structural, physical, pharmacological, or chemical characteristics of a disease-causing substance in a sample. Structural properties include, but are not limited to, whether the disease-causing substance is crystalline or amorphous, and if crystalline, the polymorphic form and a description of the crystal habit. Structural properties also include the composition, such as whether the disease-causing substance is a hydrate, solvate, or a salt and whether the substance is mineralized, the degree of mineralization, and identity of the minerals.

Another important structural property is the surface-to-volume ratio and the degree of agglomeration of the particles. Surface-to-volume ratio decreases with the degree of agglomeration. It is well known that a high surface-to-volume ratio improves the solubility rate and ease of bodily elimination of a disease-causing substance. Small-size particles have high surface-to-volume ratio. The surface-to-volume ratio is also influenced by the crystal habit, for example, the surface-to-volume ratio increases from spherical shape to needle shape to dendritic shape. Porosity also affects the surface-to-volume ratio, for example, disease-causing substances having channels or pores (e.g., inclusions, such as hydrates and solvates) have a high surface-to-volume ratio.

Still another structural property is particle size and particle-size distribution. For example, depending on concentrations, the presence of inhibitors or impurities, and other conditions, particles can form from solution in different sizes and size distributions. Particulate matter, produced by precipitation or crystallization, has a distribution of sizes that varies in a definite way throughout the size range. Particle- and crystal-size distribution is generally expressed as a population distribution relating to the number of particles at each size. In disease-causing substances, particle and crystal size distribution have very important clinical aspects. For example, smaller particles are more easily eliminated from the body and have higher surface-to-volume ratio that allows easier dissolution in bodily fluids. Thus, compounds or compositions that promote small crystal size can be of clinical importance in treating or preventing diseases caused by solid deposits in the body.

Pharmacological properties include, but are not limited to, toxicity and metabolic profile.

Physical properties include, but are not limited to, melting point, solubility, strength, hardness, compressibility, compactability, and resistance to energy forms, such as ultrasound, shock waves, and laser energy. Physical stability refers to a compound's or composition's ability to maintain its physical form, for example maintaining particle size; maintaining crystal or amorphous form; maintaining complexed form, such as hydrates and solvates; resistance to absorption of ambient moisture; and maintaining of mechanical properties, such as compressibility and flow characteristics. Methods for measuring physical stability include spectroscopy, sieving or testing, microscopy, sedimentation, stream scanning, and light scattering. Polymorphic changes, for example, are usually detected by differential scanning calorimetry or quantitative infrared analysis. For a discussion of the theory and methods of measuring physical stability see Fiese et al., in *The Theory and Practice of Industrial Pharmacy*, 3rd ed., Lachman L.; Lieberman, H. A.; and Kanig, J. L. Eds., Lea and Febiger, Philadelphia, 1986 pp. 193–194 and *Remington's Pharmaceutical Sciences*, 18th Edition, ed. Alfonso Gennaro, Mack Publishing Co. Easton, Pa., 1995, pp. 1448–1451, both of which are incorporated herein by reference. Flow properties of particles through liquids is also a relevant physical property. For instance, flow properties of disease-causing solids in bodily fluids and compartments dictates the distribution in and ease of elimination from the body. In but one example, red blood cells deformed by sickle-cell protein have very poor flow characteristics through capillaries. In precipitates and crystals, flow properties can be influenced by a number of factors, such as size and size distribution, shape, habit, polymorph, and porosity, etc.

Chemical properties include, but are not limited to chemical stability, such as susceptibility to oxidation and reactivity with other compounds, such as acids, bases, or chelating agents. Chemical stability refers to resistance to chemical reactions induced, for example, by heat, ultraviolet radiation, moisture, chemical reactions between components, or oxygen. Well known methods for measuring chemical stability include mass spectroscopy, UV-VIS spectroscopy, HPLC, gas chromatography, and liquid chromatography-mass spectroscopy (LC-MS). For a discussion of the theory and methods of measuring chemical stability see Xu et al, *Stability-Indicating HPLC Methods for Drug Analysis* American Pharmaceutical Association, Washington D.C. 1999 and *Remington's Pharmaceutical Sciences,* 18th Edition, ed. Alfonso Gennaro, Mack Publishing Co. Easton, Pa., 1995, pp. 1458–1460, both of which are incorporated herein by reference.

5.1.8 Physical State

According to the invention described herein, the "physical state" of a substance, such as a component or a disease-causing substance is initially defined by whether it is in solid, liquid, or dissolved form.

If the substance is a solid, the physical state is further defined by the particle or crystal size, the particle-size distribution, the degree of agglomeration and the habit.

Physical state can further be defined by purity of the solid substance, for example, whether the substance is mineralized, the degree of mineralization, and identity of the minerals. Mechanisms by which impurities can be incorporated in solid substances include surface absorption and entrapment in cracks and crevices, especially in agglomerates and crystals.

Physical state includes whether the substance is crystalline or amorphous. If the substance is crystalline, the physical state is further divided into: (1) whether the crystal matrix includes a co-adduct; (2) morphology, i.e., crystal habit; and (3) internal structure (polymorphism). In a co-adduct, the crystal matrix can include either a stoichiometric or non-stoichiometric amount of the adduct, for example, a crystallization solvent or water, i.e., a solvate or a hydrate.

Non-stoichiometric solvates and hydrates include inclusions or clathrates, that is, where a solvent or water is trapped at random intervals within the crystal matrix, for example, in channels.

A stoichiometric solvate or hydrate is where a crystal matrix includes a solvent or water at specific sites in a specific ratio. That is, the solvent or water molecule is part of the crystal matrix in a defined arrangement. Additionally, the physical state of a crystal matrix can change by removing a co-adduct, originally present in the crystal matrix. For example, if a solvent or water is removed from a solvate or a hydrate, a hole is formed within the crystal matrix, thereby forming a new physical state. Such physical states are referred to herein as dehydrated hydrates or desolvated solvates.

The crystal habit is the description of the outer appearance of an individual crystal, for example, a crystal may have a cubic, tetragonal, orthorhombic, monoclinic, triclinic, rhomboidal, or hexagonal shape.

The internal structure of a crystal refers to the crystalline form or polymorphism. A given compound may exist as different polymorphs, that is, distinct crystalline species. In general, different polymorphs of a given compound are as different in structure and properties as the crystals of two different compounds. Solubility, melting point, density, hardness, crystal shape, optical and electrical properties, vapor pressure, and stability, etc. all vary with the polymorphic form.

5.2 Technology for Producing and Screening Arrays

The array technology described herein is a high-throughput approach that can be used to generate large numbers (greater than 10, more typically greater than 50 or 100, and more preferably 1000 or greater samples) of parallel small scale samples.

5.2.1 System Design For Preparing and Screening Arrays

The basic requirements for array and sample preparation and screening thereof are: (1) a distribution mechanism to add components and the medium to separate sites, for example, on an array plate having sample wells or sample tubes. Preferably, the distribution mechanism is automated and controlled by computer software and can vary at least one addition variable, e.g., the identity of the component(s) and/or the component concentration, more preferably, two or more variables. Such material handling technologies and robotics are well known to those skilled in the art. Of course, if desired, individual components and the medium can be placed at the appropriate sample site manually. This pick and place technique is also known to those skilled in the art. And (2) a screening mechanism to test each sample to detect a change in physical state or for one or more properties. Preferably, the testing mechanism is automated and driven by a computer. Preferably, the system further comprises a processing mechanism to process the samples after component addition.

5.2.2 Preparing Arrays

An array can be prepared, processed, and screened as follows. The first step comprises selecting the medium and component sources, preferably, at one or more concentrations. Preferably, at least one component source can deliver a disease-causing substance. That is, one component source should comprises at least one of: a disease-causing substance in undissolved form; a disease-causing substance in dissolved form; or the components necessary—in dissolved or undissolved form—to induce a disease-causing substance. Next, adding the medium and the components to a plurality of sample sites, such as sample wells or sample tubes on a sample plate to give an array of unprocessed samples. The array can be processed according to the purpose and objective of the experiment, and one of skill in the art will readily ascertain the appropriate processing conditions. For example, the samples can be processed by heating, cooling, adding additional components, such as acids or bases, stirring, milling, filtering, centrifuging, emulsifying, or by simply allowing the samples to stand for a period of time at a specified temperature, for example, at normal human-body temperature. Each sample in array can be screened to determine the presence or absence of a disease-causing substance and thereafter testing the disease-causing substance for one or more properties. The data so collected is stored for subsequent data analysis, preferably, by a computer.

Preferably, the automated distribution mechanism used in accordance with the invention can distribute or add components in the form of liquids, solids, semi-solids, gels, foams, pastes, ointments, suspensions, or emulsions. Solids can be in any form, for example, powders, tablets, or pellets.

Where the components are solids—for example, nucleating inhibitors, pharmaceuticals, etc. or a component designed to mimic one or more of the properties of a particular disease-causing substance (e.g., calcium phosphate)—preferably, they are in the form of micropellets or microtablets, prepared by micropelleting or microtableting. In another embodiment, when the solid is a disease-causing substance, it can be in is natural form, i.e., as isolated from an animal, plant, cell, or tissue, for example, animal gall stones, kidney stones, protein deposits, or dental buildup. Micropellets can be prepared using standard pharmaceutical-tableting machines, modified as appropriate. Such machines are well known in the art, for example, see *Remington: The Science and Practice of Pharmacy*, Alfonso R. Gennaro ed., Mack Publishing Co. Easton, Pa., 19th ed., 1995, Chapter 92, incorporated herein by reference. Preferably, the tableting machine comprises a small die, of from about 1/16" to about 3/16" in diameter. Any required modifications are easily made by those skilled in the art. With the appropriate modification, the microtableting machine can make microtablets of almost any solid component. When the component is a pharmaceutical, it can be dispersed within a matrix of a compressible, inert carrier material, such as potassium chloride or pelleted in the absence of an inert carrier.

Another method of forming micropellets involves forcing a paste comprising a component or a component mixed with an inert carrier into a mold, drying the paste, and then ejecting the pellet. In this method, the component to be pelleted is first homogenized with a solvent or a solvent and an inert carrier. Preferably, when an inert carrier is used, it is lactose or mannitol. Any solvent is suitable and readily selected by one skilled in the art depending on the component. Preferably, the solvent is relatively volatile, more preferably having a boiling point of less than 100° C., for example, alcohols such as methanol or ethanol. Preferably, the ratio of solvent to component/inert carrier mixture is of from about 10:1 to about 1:10, more preferably about 6:1 to about 1:1, even more preferably, from about 5:1 to about 3:1. The component, solvent, and inert carrier if present are homogenized to a paste and the solvent is then removed at reduced pressure to yield a dry powder. The powder is then mixed with another solvent, preferably water, to form a homogeneous paste, which paste is forced into individual tube shaped molds. Preferably, the dimensions of the molds is from about 1/16" to about 3/16" in depth, preferably, about 1/8" in depth and from about 1/32" to about 1/8" in inner diameter, preferabl inner diameter. The pastes are allowed to dry for about 1 minute to about 5 hours, preferably, for about 5 minutes to about 1 hour, more preferably, for about 10 minutes; at a temperature of from about 15° C. to about 100° C., more preferably, from about 20° C. to about 30° C.; at a pressure of from about 10 mm/Hg to about 1000 mm/Hg, preferably, at about 20 mm/Hg. Preferably, the paste-in-mold is allowed to dry for about 10 minutes, at about room temperature, and at about atomospheric pressure. The dried paste in the form of a micropellet is then ejected from the molds, preferably, by inserting a flat head pin through the mold, the pin being of about the same diameter, preferably of just a slightly smaller diameter than the inner diameter of the mold. The molded micropellets can then be dried under reduced pressure, preferably, for from about 6 to about 24 hours, more preferably, about 12 hours; at a temperature of from about 15° C. to about 100°0 C., preferably at about room temperature; and at a pressure of from about 10 mm/Hg to about 1000 mm/Hg, preferably, about 20 mm/Hg.

A preferred automated mechanism for adding solid components, preferably micropellets, to sample sites comprises reservoirs or bins, for each component. The outlet of these bins is controlled so that an individual microtablet is "singulated" and able to be dispensed to a specified sample site in an array. Once the component(s) are distributed in the array, the assay process continues as outlined below.

In one embodiment, a system where a solid component source, such as a disease-causing-solid source or a solid-component source and a liquid-distribution source, such as a medium source or a liquid-component source, automatically distribute the respective solids or liquids to the sample sites, such as sample wells in a 96 well filter plate (commercially available, for example, from Millipore, Bedford, Mass.) to give a plurality of samples. The combinations of the medium and various components at various concentrations or combinations are generated using standard software (e.g., Matlab software, commercially available from Mathworks, Natick, Mass.). The combinations thus generated can be downloaded into a spread sheet, such as Microsoft EXCEL. From the spread sheet, a worklist can be generated for instructing the automated distribution mechanism to prepare an array of samples according to the various combinations generated by the formulating software. The worklist can be generated using standard programming methods according to the automated distribution mechanism employed. The use of so-called worklists simply allows a file to be used as the process command rather than discrete programmed steps. The worklist combines the formulation output of the formulating program with the appropriate commands in a file format that directly readable by the automatic distribution mechanism. Preferably, the automated distribution mechanism can deliver multiple amounts of each component.

Automated liquid distribution mechanisms are well known and commercially available, such as the Tecan Genesis, from Tecan-US, RTP, North Carolina. Automated solid distribution mechanisms are readily obtained by modifying commercially available robotics systems.

After dispensing is complete the plates can be sealed, if desired, to prevent evaporation or to protect the sample contents from air or light. The sealing mechanism can be a glass plate with an integrated chemically compatible gasket. This mode of sealing allows visual inspection of each sample.

5.2.3 Processing Arrays

The array thus prepared can then be processed according to the design and objective of the experiment. One of skill in the art will readily ascertain the appropriate processing conditions. Processing includes mixing; agitating; heating; cooling; adjusting the pressure; adding additional components, such as acids or bases; stirring; milling; filtering; centrifuging, emulsifying, subjecting one or more of the samples to mechanical stimulation; ultrasound; shock waves; or laser energy; or allowing the samples to stand for a period of time at a specified temperature; for example, normal human-body temperature.

In one embodiment, the array can be processed by heating to a temperature (T1), preferably to a temperature at which the all the solids are completely in solution. The samples are then cooled, to a lower temperature T2, usually for at least one hour. The presence of solids is then determined.

In another embodiment, the samples can be processed by introducing a nucleation event. Nucleation events include mechanical stimulation and exposure to sources of energy, such as acoustic (ultrasound), electrical, or laser energy. Nucleation can also be induced by adding components that decrease the surface energy. During cooling, each sample is analyzed for the presence of solid formation. This analysis allows determination of the recipitation or crystallization temperature.

Advantageously, samples in commercially available microtiter plates, can be screened for the presence of solids (e.g., precipitates or crystals) using automated plate readers. Automated plate readers can measure the extent of transmitted light across the sample. Diffusion (reflection) of transmitted light indicates the presence of a precipitate. Visual examination of these plates can also be used to detect the presence of solids. In yet another method to detect solids, the plates can be scanned for precipitation by measuring turbidity.

If desired, samples containing solids can be filtered to separate the solids from the medium, resulting in an array of filtrates and an array of solids. For example, the filter plate comprising the suspension is placed on top of a receiver plate containing the same number of sample wells, each of which corresponds to a sample well on the filter plate. By applying either centrifugal or vacuum force to the filter plate over receiver plate combination, the liquid phase of the filter plate is forced through the filter on the bottom of each sample well, into the corresponding sample well of the receiver plate. The appropriated centrifuge is available commercially, for example, from DuPont, Wilmington, Del. The receiver plate is designed for analysis of the individual filtrate samples.

5.2.3.1 Temperature

Different temperatures can be used during the solid growth phase. Typically, several distinct temperatures are tested during solid precipitation and crystal nucleation. Temperature can be controlled in either a static or dynamic manner. Static temperature means that a set incubation temperature is used throughout the solid formation process. Alternatively, a temperature gradient can be employed. For example, the temperature is decreased or raised at a constant rate throughout the solid formation.

Stand-alone devices employing Peltier-effect cooling and joule-heating are commercially available for use with microtiter plate footprints. A standard thermocycler used for PCR, such as those manufactured by MJ Research or PE Biosystems, can also be used to accomplish the temperature control. The use of these devices, however, necessitates the use of conical vials of conical bottom micro-well plates. If greater throughput or increased user autonomy is required then full-scale systems such as the advanced Chemtech Benchmark Omega 96TM or Venture 596 TM would be the platforms of choice. Both of these platforms utilize 96-well reaction blocks made from Teflon™. These reaction blocks can be rapidly and precisely controlled from −70 to 150° C. with complete isolation between individual wells. Also, both systems can operate under an inert atmosphere and utilize chemically-inert handling elements. The Omega 496 system has simultaneous independent dual coaxial probes for liquid handling, while the Venture 596 system has 2 independent 8-channel probe heads with independent z-control. Moreover, the Venture 596 system can process up to 10,000 reactions simultaneously. Both systems offer complete autonomy of operation.

5.2.3.2 Control of Saturation

Supersaturation is the thermodynamic driving force for both crystal nucleation and growth and thus is a key variable in processing arrays. Supersaturation is defined as the deviation from thermodynamic solubility equilibrium. Thus the degree of saturation can be controlled by temperature and concentrations and identities of components. In general, the degree of saturation can be controlled in the metastable region, when the metastable limit has been reached, nucleation will be induced.

5.2.3.3 Control of Nucleation

Crystal nucleation is the formation of a crystal solid phase from a liquid or amorphous phase. Nucleation sets the character of the crystallization process. So called primary nucleation can occur by heterogenous or homogeneous mechanisms. Primary nucleation does not involve existing crystals, but results from spontaneous crystal formation. Primary nucleation can be induced by increasing the saturation over the metastable limit or, when the degree of saturation is between supersaturation and the metastable, by introducing a nucleation event. Nucleation events include mechanical stimulation and exposure to sources of energy, such as acoustic (ultrasound), electrical, or laser energy. Primary nucleation can also be induced by adding primary nucleation promoters, that is substances other than the substance to be crystallized. Additives that decrease the surface energy of the compound to be crystallized can induce nucleation. A decrease in surface energy favors nucleation, since the barrier to nucleation is caused by the energy increase upon formation of a solid-liquid surface. Thus, in the current invention, nucleation can be controlled by adjusting the interfacial tension of the crystallizing medium by introducing surfactant-like molecules either by pre-treating the sample tubes or sample wells or by direct addition. The nucleation effect of surfactant molecules is dependent on their concentration and thus this parameter should be carefully controlled. Such tension adjusting additives are not limited to surfactants. Many compounds that are structurally related to the compound to be crystallized can have significant surface activity. Other heterogeneous nucleation inducing additives include solid particles of various substances, such as solid-phase excipients or impurities. Similarly, inorganic crystals on specifically functionalized self-assembled monolayers (SAMs) have also been demonstrated to induce nucleation by Wurm, et al. ,1996, *J. Mat. Sci. Lett.* 15:1285 (1996). Nucleation of organic crystals such as 4-hydroxybenzoic acid monohydrate on a 4-(octyldecyloxy)benzoic acid monolayer at the air-water interface has been demonstrated by Weissbuch, et al. 1993 *J. Phys. Chem.* 97:12848 and Weissbuch, et al., 1995 *J. Phys. Chem.* 99:6036. Nucleation of ordered two dimensional arrays of proteins on lipid monolayers has been demonstrated by Ellis et al., 1997, *J. Struct. Biol.* 118:178.

Secondary nucleation involves treating the crystallizing medium with a secondary nucleation promoter, that is crystals of the compound to be crystalized itself. Direct seeding of samples with a plurality of nucleation seeds in various physical states provides a means to induce formation of different crystal forms. In one embodiment, particles are added to the samples. In another, nanometer-sized crystals (nanoparticles) are added to the samples.

5.2.3.4 Control of Particle Size

As discussed above, particle size is very relevant to the clinical aspects of disease-causing solids. Particle size and size distribution often dictate the pathology of disease-causing solids. The body has variable responses to pathogenic particles depending on size and size distribution, such as immune response and whether osteocytes or macrophages are activated. Particulate matter, produced by precipitation or crystallization, has a distribution of sizes that varies in a definite way throughout the size range. Particle- and crystal-size distribution is generally expressed as a population distribution relating to the number of particles at each size. In disease-causing substances, particle and crystal size distribution have very important clinical aspects. For example, smaller particles are more easily eliminated from the body and have higher surface-to-volume ratio that allows easier dissolution in bodily fluids. The particle size of substances formed by crystallization or precipitation from solvents or other fluids, such as bodily fluids, is influenced by a number of factors, such as nucleation, number of nucleation sites, degree of saturation of the substance, solubility of the substance. The structure of the formed precipitate or crystals also influences particle size and size distribution. Structural properties, such as habit, polymorph, porosity, and composition can affect crystal size in many ways, such as providing additional nucleation sites and affecting the growth rate.

5.2.3.5 Time

Samples can be incubated for various lengths of time. Since physical-state changes, particularly crystallizations, can occur as a function of time, it is advantageous to examine arrays over a range of times.

5.2.3.6 pH

The charge of the compound being precipitated or crystallized can determine the nature of the solid phase that is generated. The pH can be modified by the addition of inorganic and organic acids and bases, additional crystallization additives such as small molecules, macromolecules, and solvents.

5.2.3.7 Solvent Composition

The use different solvents or mixtures of solvents can inhibit or promote physical-state changes and influence the type of physical state change, such as whether crystals or a precipitate is generated. Solvents may influence and direct the formation of the solid phase through electrostatic properties, charge distribution, molecular shape and flexibility, and pH. Solvents accepted for use in drug manufacture are preferred for use in the arrays of the invention. Various mixtures of those solvents can be used. Solvents include, but are not limited to, aqueous-based solvents such as water, aqueous acids, bases, salts, and buffers or mixtures thereof and organic solvents, such as protic, aprotic, polar or nonpolar organic solvents.

5.2.3.8 Concentration of the Components

The concentration of the components can influence, promote, or inhibit changes in physical state, for example, whether a crystal or a precipitate is formed. The temperature at which crystallization is thermodynamically possible is generally a strong function concentration. Crystal-growth rate increases with increasing concentration, which can affect crystal habit. For example, rapid growth must accommodate the release of the heat of crystallization. This heat effect is responsible for the formation of dendrites during crystallization. The macroscopic shape of the crystal is profoundly affected by the presence of dendrites and even secondary dendrites. Another effect of concentration of components is the chemical composition of the crystal or precipitate formed. For example, a concentrated solution may first form crystals of the hemihydrate when precipitated from aqueous solution at high temperature. The dihydrate may, however, be the first to form when starting with a dilute solution.

5.2.3.9 Viscosity and Rheology

The viscosity and rheology of biomolecules is an important target for providing treatment in various disease states. Influencing, modifying, promoting, or inhibiting changes in physical state, for example, can modulate viscosity and Theological properties in a desirable manner. For instance, microtubules interconvert stochastically between polymerization and depolymerization of tubulin. Substances affecting microtubule dynamics, such as paclitaxel and colchicin, have important therapeutic properties. Kinoshita et al., 2001, *Science*, 294:1340, demonstrate with the aid of reconstitution experiments that two factors in addition to tubulin account for the 'high catastrophe' rates, i.e., depolymerization, in microtubules as well as the observed 'rescue' rates, i.e., polymerization.

The ability to observe catastrophe and rescue in vitro, for instance as described by Kinoshita et al., allows screening for additional compounds suitable for inducing polymerization or depolymerization of microtubule to further expand the useful known drugs for combating cancers such as leukemia among other conditions. Thus, the methods of the invention encompass high-throughput screening for compounds that induce polymerization or depolymerization of microtubules, and the use of certain compounds identified by the methods of the invention to treat diseases associated with microtubule polymerization.

Another example of importance of rheological properties is provided by the accumulations in the lungs of patients suffering from cystic fibrosis. A significant reason for the failure to effectively clear the lungs of such patients is the viscosity of the secretions due to the presence of deoxyribonucleic acid (DNA) and actin due to residual matter left from repeated infections, for instance discussed by Griese et al., 1997, *Pulm. Pharmacol. Ther.*, 10:21. Screening for compounds that, for example, weaken the association between actin and DNA filaments would greatly aid in reducing the viscosity of such secretions and their clearance. Zahm et al., 2001, *Am. J. Respir. Crit. Care Med.*, 163:1153 Moreover, such compounds may further increase the efficacy of DNase administered to lower the viscosity for more effective clearance of the airways. Thus, more effective formulations of DNase and other treatments are possible by screening methods taught by the instant application. The methods of the invention encompass high-throughput screening for compounds that induce dis-aggregation of DNA, and the use of certain compounds identified by the methods of the invention to treat diseases associated with DNA aggregation.

Rheological properties of human semen provide yet another example of the application of such considerations in a biological context is provided by human semen. Human semen exhibits high viscosity and an almost gel like behavior soon after ejaculation, see, e.g., Dunn et al., 1977, *Int. J. Infertil*, 22:217. Mandal et al., 1985, Andrologia, 17:228 describe the liquefaction of the ejaculate coagulum with modification of fibers into globular bodies that fuse to form the homogenous liquified semen. This process is known to include several steps, e.g., Koren et al., 1979, *J. Reprod. Fertil.*, 56:493, while, Chatterjee et al., 1997, *Arch. Androl*, 38:107, describe aminopeptidase and amylase as the major liquefying factors. Thus, the methods of the invention encompass high-throughput screening for compounds that modulate liquefaction of human semen, and the use of certain compounds identified by the methods of the invention to treat diseases associated with semen liquifaction.

Screening for safe and effective inhibitors of the liquefaction by assaying the flow properties of a semen-coagulum in accordance with the described invention can yield safer and effective compounds and formulations with many applications. Such compounds and formulations can be provided, for instance, externally in suppositories or creams and the like, for providing birth control since liquefaction is required for further migration of sperms in the female reproductive system following deposition therein. Interestingly, compounds and formulations promoting liquefaction of the sperm-coagulant are also useful as a potentially safe aid for increasing the likelihood for pregnancy and are likely to be readily identified by screens in accordance with the invention described herein. Thus, the methods of the invention encompass high-throughput screening for compounds that induce liquefaction of human semen, and the use of certain compounds identified by the methods of the invention to treat diseases and conditions associated with semen to liquefaction.

5.2.4 Screening Arrays

After processing, the samples are analyzed to detect those samples wherein a change in physical state occurred. In one embodiment, the sample's filtrate can be analyzed to detect or measure concentrations of dissolved substances, for example, the concentration of a dissolved disease-causing solid. Solubility can be analyzed using devices, such as UV-Vis spectroscopy (using plate-based readers known to those skilled in the art, an example of which is the SpectraMax Plus from Molecular Devices, Sunnyvale, Calif.), GC, HPLC, and LC-MS. In the case of GC, HPLC, and LC-MS, an automated pipetting station is used for sample introduction, for example, the Genesis from Tecan or any of several devices sold by Gilson, Middleton, Wis.).

In another embodiment, solid materials present in the samples are analyzed, such as solid disease-causing substances. Suitable methods of analysis include, but are not limited to, x-ray diffraction crystallography, such as single crystal or powder x-ray diffraction; second harmonic generation (SGH); microscopy; photomicrography; thermal methods of analysis, such as thermogravimetric analysis (TGA) and differential thermal analysis (DTA); electron microscopy; infrared spectroscopy; and analytical methods requiring dissolution of the solid, such as ultraviolet spectroscopy, nuclear magnetic resonance (NMR) spectroscopy; polarography; gas chromatography; and high-pressure liquid chromatography (HPLC). Solids can also be analyzed by subjecting them to energy forms, such as laser, ultrasound, or shock waves to determine their resistance thereto.

Other analytical devices that can be used with the methods and arrays of the invention include pH sensors, ionic strength sensors, optical spectrometers, devices for measuring turbidity, calorimeters, infrared spectrometers, polarimeters, radioactivity counters, conductivity measurers, and heat of dissolution measurers.

Data collection and storage preferably, are performed by computers using the appropriate software. Such computers and software are readily chosen by one of skill in the art. The data is typically collected and stored directly from the analytical equipment using software provided by the instrumentation's manufacturer. The data set can then be downloaded to a database for analysis.

Data analysis can be performed using visualization software, such as SPOTFIRE (commercially available from Spotfire, Inc., Cambridge, Mass.). The visualized data can be analyzed directly to arrive at optimized conditions, compounds, or compositions. Or the data can be processed through data mining algorithms so as to optimize the ability of scientific personnel to detect complex multi-dimensional interactions or lack of interactions between components or to conduct future experiments to optimize the formulations. Examples of suitable data-mining software include, but not limited to, SPOTFIRE; MATLAB (Mathworks, Natick, Mass.); STATISTICA (Statsoft, Tulsa, Okla.). All resulting analysis files are stored on a central file server, i.e., a data base, where the files can be accessed by traditional means known to those skilled in the art.

5.2.4.1 Analysis of Solids

In certain embodiments, after processing solids, such as solid disease-causing substances generated samples can be detected and analyzed. There are several general methods applicable. After a solid is detected it can be further analyzed to define its physical state.

In the preferred embodiment, so-called machine vision technology is used. Specifically, images are captured by a high-speed charge-coupled device (CCD) camera that has an on-board signal processor. This on-board processor is capable of rapid processing of the digital information contained in the images of the sample tubes or sample wells. Typically, two images are generated for each location of the well that is being analyzed. These two images differ only in that each is generated under different incident light polarization. Differences in these images due to differential rotation of the polarized light indicates the presence of crystals. For wells that contain crystals, the vision system determines the number of crystals in the well, the exact spatial location of the crystals within the well (e.g., X and Y coordinates) and the size of each crystal. This size information, measured as the aspect ratio of the crystal, directly corresponds to crystal habit. The use of on-line machine vision to determine both the absence/presence of crystals as well as detailed spatial and morphological information has significant advantages. Firstly, this analysis provides a "filtering" means to reduce the number of samples that will ultimately undergo in-depth analysis. Secondly, the spatial information gathered on the locations of crystals is critical to the efficiency in which the in-depth analyses can be performed. This information allows for the specific analysis of individual crystals that are two to four orders of magnitude smaller than the wells that they are contained in. Those wells (reservoirs or sites in the array) identified to contain crystalline or other specific solids can then be further analyzed.

Crystallinity can be assessed automatically using plate readers with polarized filter apparatus to measure the total light to determine crystal birefringence. Plate readers are commercially available. It is also possible to monitor turbidity or birefringence dynamically throughout the crystal forming process. Precipitation, which is indicative of crystal formation, is monitored by optical density, which can be visually or spectrophotometrically determined by turbidity. Crystallinity is determined by birefringence which distinguishes crystals from amorphous material; crystals turn polarized light, while amorphous materials absorb the light. True polymorphs, solvates, and hydrates, are tested by x-ray Powder Diffraction (XRPD) (angles of diffracted laser light can be used to determine whether true polymorph(s) have been formed). Different crystalline forms are determined by differential scanning calorimetry (DSC) and Thermographic Gravimetric (TG) analysis.

5.2.4.1.1 X-Ray Diffraction

The x-ray crystallography technique, whether performed using single crystals or powdered solids, concerns structural analysis and is well suited for the characterization of polymorphs and solvates as well as distinguishing amorphous from crystalline solids. In the most favorable cases, it can lead to a complete determination of the structure of the solid and the determination of the packing relationship between individual molecules in the solid.

Single crystal x-ray diffraction is the preferred analytical technique to characterize crystals generated according to the arrays and methods of the invention. The determination of the crystal structure requires the determination of the unit-cell dimensions and the intensities of a large fraction of the diffracted beams from the crystal.

The first step is selection of a suitable crystal. Crystals should be examined under a microscope and separated into groups according to external morphology or crystal habit. For a complete study, each crystal of a completely different external morphology should be examined.

Once the crystals have been separated according to shape, the best crystal of the first group should be mounted on a goniometer head with an adhesive such as glue.

The unit cell dimension are then determined by photographing the mounted crystal on a precession camera. The unit cell parameters are determined from the precession photograph by measuring the distance between the rows and columns of spots and the angle between a given row and column. This is done for three different orientations of the crystal, thus allowing determination of the unit cell dimensions.

The intensities of the diffracted radiation are most conveniently measured using an automated diffractometer that is a computer-controlled device that automatically records the intensities and background intensities of the diffracted beams on a magnetic tape. In this device, the diffracted beam is intercepted by a detector, and the intensity is recorded electronically.

The diffraction data are then converted to electron density maps using standard techniques, for example, the DENZP program package (Otwinowski, et al., Methods in Enzymology 276 (1996)). Software packages, such as XPLOR (A. Brunger, X-PLOR Manual, Yale University), are available for interpretation of the data. For more details, see Glusker, J. P. and Trueblood, K. N. "Crystal Structure Analysis", Oxford University Press, 1972.

X-ray Powder Diffraction can also be used. The method that is usually used is called the Debye-Scherrer method (Shoemaker and Garland, 1962). The specimen is mounted on a fiber and placed in the Debye-Scherrer powder camera. This camera consists of an incident-beam collimator, a beam stop, and a circular plate against which the film is placed. During the recording of the photograph, the specimen is rotated in the beam. Because the crystallites are randomly oriented, at any given Bragg angle, a few particles are in diffracting position and will produce a powder line whose intensity is related to the electron density in that set of planes.

This method, along with precession photography, can be used to determine whether crystals formed under different conditions are polymorphs or merely differ in crystal habit. To measure a powder pattern of a crystal or crystals on a Debye-Scherrer camera, one grinds the sample to a uniform size (200–300 mesh). The sample is then placed in a 0.1- to 0.5-mm-diameter glass capillary tube made of lead-free glass. Commercially made capillary tubes with flared ends are available for this purpose. The capillary tube is placed on a brass pin and inserted into the pin-holder in a cylindrical Debye-Scherrer powder camera. The capillary tube is aligned so that the powdered sample remains in the x-ray beam for a 360° rotation. Film is then placed in the camera, and the sample is exposed to $CuK_\alpha$ x-rays. The film is then developed and the pattern is compared to the pattern from other crystals of the same substance. If the patterns are identical the crystals have the same internal structure. If the patterns are different, then the crystals have a different internal structure and are polymorphs.

5.2.4.1.2 Second Harmonic Generation (SHG)

Symmetry lowering in host-additive systems (crystals incorporating guest molecules, e.g., solvates), such as a loss of inversion, glide, or twofold screw symmetry, which would introduce polarity into the crystal, can be probed by non-linear optical effects, such as second harmonic generation, which is active in a noncentrosymmetric crystalline forms. For a comprehensive review on second harmonic generation see Corn et al., 1994 *Chem. Rev.* 94:107–125.

5.2.4.1.3 Microscopy and Photomicrography

This method of analysis involves observation of crystals and physical-state changes of crystals under a microscope (Kuhuert-Brandstatter, 1971). Crystals are usually placed on a microscope slide and covered with a cover slip. However, sometimes a steel ring with input and output tubes is used to control the atmosphere. The microscope slide is often placed on a "hot stage," a commercially available device for heating crystals while allowing observation with a microscope. The heating rate of crystals on a hot stage is usually constant and controlled with the help of a temperature programmer.

Crystals are often photographed during heating. Photography is helpful because for solid-state changes taking weeks to complete it is sometimes difficult to remember the appearance of a crystal during the entire change.

The following types of behavior are of particular interest to the solid-state chemist:

1. The loss of solvent of crystallization.
2. Sublimation of the crystal—the crystal slowly disappears and condenses on the cover slip.
3. Melting and re-solidification, indicating a phase change (polymorphic transformation) or solid-state change.
4. Chemical reaction characterized by a visible change in the appearance of the crystal.

The detection of loss of solvent of crystallization and phase or polymorphic transformations is important to the solid-state chemist, since crystals exhibiting this behavior can have different reactivity and different bioavailability.

5.2.4.1.4 Thermal Methods of Analysis

Thermal analysis generally refers to any method involving heating the sample and measuring the change in some physical property. The most important thermal methods for the study of solid-state chemistry are thermogravimetric analysis (TGA) and differential thermal analysis (DTA). Thermogravimetric analysis involves measuring the change in the mass of the sample as the temperature is changed. Differential thermal analysis involves measuring the difference between the temperature of the sample and a reference compound as the temperature is changed, and provides information on the enthalpy change of various solid-state processes.

Thermogravimetric Analysis (TGA) involves the measurement of the change in mass with temperature and is often used to study the loss of solvent of crystallization or other solid→solid+gas changes. In studies of solid-state chemistry, TGA is usually performed in one of two modes: isothermal or dynamic. In the isothermal mode, the temperature is constant, while in the dynamic mode the temperature is raised at a constant rate. There are a number of factors that affect TGA curves, including the heating, atmosphere, crystal size of the sample, nature of the change, treatment of the sample, and thermal conductivity of the sample. The affect of the heating rate has been extensively studied (Wendlandt, 1974). In general, as the heating rate is increased, the starting temperature of the thermal event ($T_i$) increases. However, this condition can sometimes be corrected by decreasing the sample size. The atmosphere can have a dramatic effect on the TGA curve. For example, an atmosphere containing the product gas can increase $T_i$ or stop the change completely. In addition, the atmosphere can change the course of the change, particularly if the atmospheric gas reacts with either the products or the reactant. In general, the crystal size of the sample has a predictable effect on the TGA curve. The smaller the crystal size, the faster the physical change and the lower the value of $T_i$. This is because the small crystals have relatively large surface areas, and more rapid escape of the produce gas is allowed. Obviously, the nature of the change effects $T_i$. The $T_i$ is lower for the more facile physical changes. In addition, the extent of compression of the sample will affect the $T_i$. For example, increased compression will increase $T_i$ since the product gas will have fewer opportunities to escape. Finally, the thermal conductivity of the sample will influence $T_i$ and could lead to anomalous effects if the temperature of the sample is not uniform. The rates of physical changes of the type solid→solid+gas can be determined using TGA. Obviously, TGA traces can be used to determine the rate of the physical change and the rate law governing the physical change.

Dynamic TGA has also been used to determine the rates of solid→solid+gas physical changes. However, in general, the kinetic data obtained should be substantiated by other data before it is considered absolutely correct. It should be noted that the use of dynamic TGA to study kinetics has been criticized.

Isothermal thermogravimetric analysis has been used extensively to study the desolvation of crystal solvates.

Differential Thermal Analysis (DTA) is a method in which the temperature of the sample ($T_s$) is compared to the temperature of a reference compound ($T_v$) as a function of increasing temperature. Thus, a DTA thermogram is a plot of $\Delta T = T_s - T_v$ (temperature difference) versus T. The endotherms represent processes in which heat is absorbed, such as phase transitions and melting. The exotherms represent processes such as chemical reactions where heat is evolved. In addition, the area under a peak is proportional to the heat change involved. Thus, this method with proper calibration can be used to determine the heats ($\Delta H$) of the various processes, the temperatures of processes such as melting, $T_m$, can be used as an accurate measure of the melting point.

There are a number of factors that can affect the DTA curve, including heating rate, atmosphere, the sample holder and thermocouple location, and the crystal size and sample packing. In general, the greater the heating rate the greater the transition temperature (i.e., $T_m$) An increased heating rate also usually causes the endotherms and exotherms to become sharper. The atmosphere of the sample affects the DTA curve in much the same way it affects the TGA curve. If the atmosphere is one of the reaction products, then increases in its partial pressure would slow down the reaction. The shape of the sample holder and the thermocouple locations can also affect the DTA trace. Thus, it is a good idea to only compare data measured under nearly identical conditions. As with TGA, the crystal size and packing of the sample has an important influence on all reactions of the type solid→solid+gas. In such reactions, increased crystal size (thus decreased surface area) usually decreases the rate of the reaction and increases the transition temperature.

DTA has been used to study the kinetics of solid-state physical changes but, like the TGA methods, this approach has been criticized and results of kinetic studies by DTA should probably be checked by other methods before they are considered reliable.

An important type of differential thermal analysis is differential scanning calorimetry (DSC). Differential Scanning Calorimetry refers to a method very similar to DTA in which the $\Delta H$ of the reactions and phase transformations can be accurately measured. A DSC trace looks very similar to a DTA trace, and in a DSC trace the area under the curve is directly proportional to the enthalpy change. Thus, this method can be used to determine the enthalpies of various processes (Curtin et al., 1969).

5.2.4.1.5 Electron Microscopy

Electron microscopy is a powerful tool for studying the surface properties of crystals. High-resolution election microscopy can be used to visualize lattice fringes in inorganic compounds, but its usefulness for visualization of lattice fringes in organic compounds is so far unproven. Nevertheless, electron micrographs of organic crystals allow the examination of the crystal surface during physical or chemical change. Electron microscopy is particularly useful for studying the affects of structural imperfections and dislocations on solid-state organic physical or chemical changes. For example, the surface photooxidation of anthracene is obvious from electron micrographs taken at a magnification of 10,000 (Thomas, 1974). Even more interesting is the use of electron microscopy, sometimes in conjunction with optical microscopy, to study the effects of dislocations and various kinds of defects on the nucleation of product phase during a solid state physical change.

Electron microscopy is also quite useful for the studies of the effect of crystal size on desolvation physical changes. Electron micrographs have significantly more depth of field than optical micrographs, so that the average crystal size can be more easily determined using them.

5.2.4.1.6 Solids Fragmentation via Laser Irradiation and Ultrasonic Waves

The particular array members that give rise to the formation of solids may also be analyzed through the use of laser or ultrasound generated shock waves. Ultrasound lithotripsy of renal stones was first reported in 1977. Lithotripsy is a process involving the fragmentation of stone through the use of a high-energy shock waves generated by a high-voltage energy source. Shock wave sources such as electrohydraulic, piezoceramic, or electromagnetic devices have been used to fragment gallbladder stones. Fauci et al., *Harrison's Principle of Internal Medicine,* 14th ed., McGraw-Hill Health Professions Division, 1998. The same shock wave sources may be adapted for use in the present invention.

Fragmentation of the solid materials that formed from the arrays may also be achieved by subjecting stones and other solid materials to laser-generated shock waves. The shock waves produced by lasers generally allow safe fragmentation of urinary calculi compared to the laser-based thermal fragmentation of stones. For clinical applications, laser-based fragmentation method requires that the shock wave energy exceed the stone's tensile strength. H. D. Fair and I. Fensel used a laser induced shock wave in 1968 instead of relying on laser thermal effect to fragment stones using a Q-switched Nd-YAG laser. Laser sources that provide short pulses generally tend to generate significantly less thermal effect than continuous wave lasers. The reduced thermal effect leads to less tissue damage. Various types and brands of continuous or pulsed lasers are commercially available (Coherent, Lambda-Physik, Spectra-Physics, etc.) and their wavelength ranges vary from the infrared to ultraviolet. Femtosecond lasers are also now widely available, in addition to the traditional nanosecond and picosecond pulsed lasers. The laser power or power density may be adjusted accordingly to determine the threshold required for fragmentation.

A holmium-YAG laser having a wavelength at 2100 nm (near infrared) has been used to fragment stones successfully. The fragmentation is based on the energy absorption and water vaporization at the stone's surface and its pores. The color and composition of the stones have been found to be irrelevant. The first commercially produced lithotriptor, HM3, was introduced in 1984. Nowadays, most non-passable upper urinary tract stones are treated with extracorporeal shock wave lithotripsy. There are now about 30 different Extracorporeal Shock Wave lithotripsy devices available, and electrohydraulic energy source is one of the most widely-used sources.

5.2.4.1.7 Raman and Infrared Spectroscopy of Solids

Raman and Infrared spectroscopy are useful methods for analysis of solids, one advantage being that it can be performed without sample dissolution. The infrared and near infrared spectrum are extremely sensitive to structure and conformation. The method involves grinding the sample and suspending it in Nujor or grinding the sample with KBr and pressing this mixture into a disc. This preparation is then placed in the near infrared or infrared sample beam and the spectrum is recorded.

Raman and Infrared spectroscopy are also useful in the investigation of polymorphs 25 in the solid state. For example, polymorphs A and B of tolbutamide give different infrared spectra (Simmons et al., 1972). It is clear that there are significant differences between the spectra of the polymorphs.

5.2.4.1.8 Ultraviolet Spectroscopy

Ultraviolet spectroscopy is very useful for studying the rates of solid-state physical changes. Such studies require that the amount of reactant or product be measured quantitatively. Pendergrass et al. (1974) developed an ultraviolet method for the analysis of the solid-state thermal physical change of azotribenzoylmethane. In this reaction, the yellow (H1) thermally rearranges to the red (H2) and white (H3) forms in the solid state. All three compounds (H1, H2, and H3) have different chromophores, so that this reaction is amenable to analysis by ultraviolet spectroscopy. Pendergrass developed a matrix-algebra method for analyzing multi component mixtures by ultraviolet spectroscopy and used it to analyze the rate of the solid-state reaction under various conditions.

5.2.4.1.9 Nuclear Magnetic Resonance (NMR) Spectroscopy

The observation of NMR spectra requires that the sample be placed in a magnetic field where the normally degenerate nuclear energy levels are split. The energy of transition between these levels is then measured. In general, the proton magnetic resonance spectra are measured for quantitative analysis, although the spectra of other nuclei are also sometimes measured.

There are three important quantities measured in NMR spectroscopy: the chemical shift; the spin-spin coupling constant, and the area of the peak. The chemical shift is related to the energy of the transition between nuclei, the spin-spin coupling constant is related to the magnetic interaction between nuclei, and the area of the peak is related to the number of nuclei responsible for the peak. It is the area of the peak that is of interest in quantitative NMR analysis.

The ratio of the areas of the various peaks in proton NMR spectroscopy is equal to the ratio of protons responsible for these peaks. For multi component mixtures, the ratios of areas of peaks from each component are proportional both to the number of protons responsible for the peak and to the amount of the component. Thus, the addition of a known concentration of an internal standard allows the determination of the concentrations of the species present. For cases where the ratio of starting material and product is desired it is not necessary to add an internal standard.

5.2.4.1.10 Polarography

Polarography is a special type of voltammetry that uses a dropping mercury electrode. In this experiment an electrochemical reaction is allowed to proceed at a given potential at the electrode and the current flow is measured. The current flow is proportional to the amount of species present. This proportionality is reflected in the well-known Ilkovic equation. Since different compounds undergo reactions at different potentials, polarography, at least in favorable cases, allows the quantitative analysis of one species in the presence of others. However, the "resolution" of polarography is significantly less than other methods such as ultraviolet or NMR spectroscopy. This is because members of one functional class of compounds (i.e., the substituted quinones) undergo electrochemical reaction at potentials close enough that significant overlap between their polarograms occurs. Polarography is sensitive to concentrations down to $10^{-5}$ to $10^{-6}$ M, depending on the functional group undergoing electrochemical reaction.

The polarographic experiment must be performed in the absence of dissolved oxygen. This is because oxygen reduction will produce a wave that obscures the reduction of most materials of interest. With water solutions, 5 min of nitrogen bubbling is usually sufficient to remove dissolved oxygen; however, organic solvents often require longer bubbling.

5.2.4.1.11 Gas Chromatography

Gas chromatography is sometimes used to study the rates and/or course of a solid state reaction. However, because the method involved both dissolving and heating the sample it has inherent drawbacks. Obviously it cannot be used to study solid-state thermal reactions, since the reaction would occur during analysis in the gas chromatography. Gas chromatography, however, is well suited for studying thermally stable materials and has found use in the study of solid-state photochemical reactions as well as desolvations and solid-state hydrolysis reactions. Gas chromatography is rapid, with a typical analysis requiring 5–30 min, and is sensitive. The sensitivity can be greatly enhanced by using a mass spectrometer as a detector.

A typical analysis proceeds in the following steps:

Step 1. A suitable stationary phase (column) is selected.
Step 2. The optimum column temperature, flow rate, and column length are selected.

Step 3. The best detector is chosen.

Step 4. A number of known samples are analyzed, a calibration curve is constructed, and the unknowns are analyzed.

5.2.4.1.12 High-pressure Liquid Chromatography (HPLC)

High-pressure liquid chromatography is probably the most widely used analytical method in the pharmaceutical industry. However, because it is a relatively new method (1965–1970), only a few minutes of its use for the study of solid-state reactions are available.

In some ways, a high-pressure liquid chromatography resembles a gas chromatography in that it has an injector, a column, and a detector. However, in high-pressure liquid chromatography it is not necessary to heat the column or sample, making this technique useful for the analysis of heat sensitive materials. In addition, a wide range of column materials are available, ranging from silica to the so-called reversed-phase columns (which are effectively nonpolar columns). As with gas chromatography, several detectors are available. The variable-wavelength ultraviolet detector is particularly useful for pharmaceuticals and for studying the solid-state reactions of drugs, since most drugs and their reaction products absorb in the ultraviolet range. In addition, extremely sensitive fluorescence and electrochemical detectors are also available.

A typical analysis by HPLC proceeds in the following manner:

Step 1. Selection of column and detector—these selections are usually based on the physical properties of the reactant and the product.

Step 2. Optimization of flow rate and column length to obtain the best separation.

Step 3. Analysis of known mixtures of reactant and product and construction of a calibration curve.

Thin-layer chromatography (TLC) provides a very simple and efficient method of separation. Only minimal equipment is required for TLC, and very good separations can often be achieved. In general, it is difficult to quantitate TLC, so it is usually used as a method for separation of compounds.

A typical investigation of a solid-state reaction with TLC proceeds as follows:

Step 1. The adsorbent (stationery phase) is selected and plates either purchased or prepared. Usually silica gel or alumina are used.

Step 2. The sample and controls, such as unreacted starting material, are spotted near the bottom of the plate and developed in several solvents until the best separation is discovered.

This procedure then gives the researcher a good idea of the number of products formed. Based on these preliminary studies, an efficient preparative separation of the products and reactant can often be designed and carried out.

5.3 Conditions, Compounds, or Compositions That Prevent or Inhibit Crystallization, Precipitation, Formation, Modification, or Deposition of Disease-Causing Substances In one embodiment, the invention is useful to discover or optimize conditions, compounds, or compositions that prevent or inhibit crystallization, precipitation, formation, modification, or deposition of disease-causing substances. Possible changes include conformational changes, changes in habit for crystals or of a propensity to aggregate or polymerize for macromolecular aggregates. In this embodiment, an array is prepared comprising samples having the appropriate medium and having either a dissolved disease-causing substance or having the components necessary—in dissolved or undissolved form—to induce a disease-causing substance. Thus, the contents of one or more of the samples is prepared to mimic the in-vivo conditions suitable for forming a disease-causing substance. Then, if desired, various components in varying concentrations are added to selected samples and the samples are processed. If desired, particular samples can be processed under various conditions. Preferably, one or more of the samples differs from one or more other samples by:

(i) the identity or an amount of the dissolved disease-causing substance;

(ii) the identity or an amount of the medium;

(iii) the identity or an amount of at least one of the components; or (iv) the pH.

For example, samples can have one or more of the following components at various concentrations: compounds and compositions that prevent or inhibit precipitation, formation, crystallization, or nucleation; compositions and compounds that promote dissolution, etching, destruction, or breakup of inorganic and organic solids; nucleation promoters; compositions or compounds that affect crystal habit; nutrients; pharmaceuticals; hormones; steroids; proteins and peptides; chelating agents; anti-dental-calculus and anti-dental-plaque agents; excipients; organic solvents; salts; acids; bases; gases; or stabilizers.

Preferably, one or more negative controls contains only the medium and components necessary to mimic the in-vivo conditions suitable to form a disease-causing substance and that does generate the disease-causing substance, thus to guaranteeing the integrity of the experiment. After processing, the samples can be analyzed to identify those samples having a disease-causing substance and those that do not. The samples that do not have disease-causing substances are predicative of conditions, compounds, or compositions that prevent or inhibit crystallization, precipitation, formation, or deposition of disease-causing substances.

The positive sample can be further analyzed to determine the disease-causing substance's structural, physical, pharmacological, or chemical properties. Structural properties include whether the solid is crystalline or amorphous, and if crystalline, the polymorphic form and a description of the crystal habit. The disease-causing substance's composition can be analyzed to determine whether it is a hydrate, solvate, or a salt or whether it is mineralized. Also, the surface-to-volume ratio and the degree of particle agglomeration can be determined. Since a high surface-to-volume ratio of particles improves their solubility rate and ease of bodily elimination, in certain contexts, disease-causing substances having a high surface-to-volume are indicative of compositions or conditions that are potentially exploitable. Other physical properties that can be measured include melting point, solubility, strength, hardness, compressibility, compactability, and resistance to energy forms, such as ultrasound, shock waves, and laser energy. Thus, the experiment can reveal conditions, compounds, or compositions that form disease-causing substances more favorable than would otherwise be formed (e.g., those of the negative control or those formed in vivo). For example, compounds, compositions, or conditions that induce formation of disease-causing substances that are easily destroyed or fragmented by ultrasound or shock waves are therapeutically exploitable.

5.4 Conditions, Compounds, or Compositions That Promote Dissolution, Destruction, or Breakup of Disease-Causing Substances In one embodiment, the invention is useful to discover or optimize conditions, compounds, and compositions that promote dissolution, destruction, or breakup of inorganic and organic solids, particularly disease-causing substances. In this embodiment, an array is prepared comprising samples having the appropriate medium and having a disease-causing substance, preferably, in solid form. Then, if desired, various components in varying concentrations are added to selected samples and the samples are processed. If desired, particular samples can be processed under various conditions. Preferably, one or more of the samples differs from one or more other samples by:
  (i) the identity or an amount of the disease-causing substance;
  (ii) the identity or an amount of the medium;
  (iii) the identity or an amount of at least one of the components; or
  (iv) the pH.

For example, samples can have one or more of the following components at various concentrations: compounds and compositions that prevent or inhibit precipitation, formation, crystallization, or nucleation; compositions and compounds that promote dissolution, etching, destruction, or breakup of inorganic and organic solids; nucleation promoters; compositions or compounds that affect crystal habit; nutrients; pharmaceuticals; hormones; steroids; proteins and peptides; chelating agents; anti-dental-calculus and anti-dental-plaque agents; excipients; organic solvents; salts; acids; bases; gases; or stabilizers.

Preferably, one or more negative controls contains only the medium and the disease-causing substance. After processing, the samples can be analyzed to identify positive samples, i.e., samples wherein the disease-causing substance changed in physical state, such as by partially or fully dissolving, by fragmenting, by increasing surface-to-volume ratio, by polymorphic shift, by change in crystal habit, or has otherwise been rendered physically, structurally, or chemically more favorable. Thus, one or more of the disease-causing substance's structural, physical, pharmacological, or chemical properties can be measured or determined. Structural properties related to solids include whether the solid is crystalline or amorphous, and if crystalline, the polymorphic form and a description of the crystal habit. The disease-causing substance's composition can be analyzed to determine whether it is a hydrate, solvate, or a salt or whether it is mineralized. Also, the surface-to-volume ratio and the degree of particle agglomeration can be determined. Since a high surface-to-volume ratio of particles improves their solubility rate and ease of bodily elimination, in certain contexts, disease-causing substances having a high surface-to-volume are indicative of compositions or conditions that are potentially exploitable. Other physical properties that can be measured include melting point, solubility, strength, hardness, compressibility, compactability, and resistance to energy forms, such as ultrasound, shock waves, and laser energy. Thus, this experiment can reveal conditions, compounds, or compositions that convert disease-causing substances to more favorable forms.

5.5 Clinical Exploitation of Conditions, Compounds, and Compositions That Inhibits, Prevent, Induce, Modify, or Reverse Transitions of Physical State Usually, the final step of the methods discussed herein is to select and further analyze samples with the most desirable properties, for example, selection and clinical exploitation of samples wherein crystallization, precipitation, formation, or deposition of disease-causing substances was prevented or inhibited, relative to a negative control; selection and clinical exploitation of samples where dissolution, destruction, or breakup of disease-causing substances was promoted, relative to a negative control; or selection and clinical exploitation of samples where formation of a desirable substance was promoted, relative to a negative control. From such samples, clinically-relevant conditions, compounds, or compositions can be identified and exploited to treat (e.g., reverse) or prevent the disease itself, the cause of the disease, or the symptoms of the disease.

Clinically relevant compounds and compositions can be assayed, for use as drugs to treat or prevent the diseases of physical-state transition mentioned in section 2.2 above. For example, the clinically relevant compounds and compositions can be assayed for effectiveness, potency, toxicity, absorption, and metabolism using in-vitro and in-vivo tests and experiments well known to those skilled in the pharmaceutical arts.

5.5.1 Illustrative Examples Addressing Diseases of Phase Transition

For clinically-relevant conditions, treatments or medicines may be identified by the arrays and methods of the invention, in conjunction with well-known methods, techniques, or pharmaceuticals. Accordingly, discussed next are illustrative exemplary embodiments of the invention.

5.5.1.1 Screening for Compounds That Delay or Inhibit Pathological Aggregations of Hemoglobin and Other Bio-Molecules of Interest As described earlier, Sickle Cell Disease is caused by a single nucleotide substitution resulting in a substitution of the amino acid Glu for Val on the sixth position of the beta-globin polypeptide chain. This seemingly minor change in amino acid composition of the globin protein causes a profound change in the solubility of deoxygenated hemoglobin containing either one or two such abnormal beta-globin molecules. Deoxygenated sickle cell hemoglobin (HbS) has a tendency to polymerize resulting in "sickling" of polymer containing erythrocytes, i.e., deformation of otherwise substantially rigid red blood cells that, in turn, causes occlusion of the microvasculature. This polymerization depends on the rate of nucleation for formation of deoxygenated hemoglobin polymers that are pathological aggregations of HbS. The rate of nucleation leading to such polymerization is lower at a reduced temperature, a property exploited in several therapeutic strategies described next.

Screening for compounds that inhibit polymerization of deoxygenated HbS is one approach to sidestep the deleterious effects of Sickle Cell Disease. Accordingly, if the time taken by deoxygenated HbS to nucleate polymers were to be made greater, for instance by administering a suitable treatment, than that required to reoxygenate HbS then the sickling phenotype could be avoided. Compounds that recognize states of HbS leading to a nucleation event are one possible category of substances that would target only the physiologically relevant form of HbS. The advantage of employing such compounds is that they are not required in large doses since they exhibit lower affinity for hemoglobin that is not in a state leading to a nucleation event. In addition, since one or a few molecules or particles of a compound of interest may prevent many more hemoglobin molecules from polymerizing, the therapeutically effective amount of such a compound should be reasonable even in view of the amount of hemoglobin to be targeted.

Such screening is possible since deoxygenated HbS takes longer to polymerize at lower temperatures. Thus, in an exemplary method, a preparation of deoxygenated HbS is maintained at a low temperature while being aliquoted and mixed with test compounds of interest. Upon raising the temperature to be within physiologically relevant temperature ranges, the aliquots exhibiting delayed polymerization indicate desired activity possessing compounds. It is noteworthy that even a small delay in nucleation is clinically significant in alleviating the disease phenotype. Moreover, if the compounds of interest have already been subjected to clinical trials, or are otherwise known compounds, then they can be rapidly subjected to further analysis to better define the new use in treating sickle cell disease condition. However, the invention is not limited to finding uses for known compounds and formulations, but includes discovery of novel compounds and formulations.

Similar screening is possible in modulating other polymerization based processes such as aggregation of fibrin in the course of blood clot formation. Modulating, e.g., preventing the formation of blood clots is desirable in many clinical settings to avoid the risk of strokes while, promoting the formation of blood clots is desirable in diseases such as hemophilia.

Another example of preventing polymerization of a substance of interest for treating a disease is provided by malaria. The well known anti-malarial chloroquine exerts its antimalarial activity through interaction with hematin in the lysosomal digestive vacuole of the malaria parasite. Presumably, this interaction compromises the ability of the parasite to adequately sequester the toxic hematin formed during proteolytic degradation of hemoglobin into hemozoin, an inert pigment. Sullivan et al., 1998, *J. Biol. Chem.*, 273: 31103–07. Based on such observations Kurosawa et al, 2000, *Antimicrobial Agents and Chemotherapy*, 44:2638, describe a high-throughput screen for identification of new antimalarial pharmacophores with the aid of a hematin polymerization assay measuring incorporation of radio-labeled hematin into insoluble polymers.

Thus, the invention encompasses high-throughput assays for identifying compounds, especially small molecules that can inhibit hemoglobin polymerization and/or be useful for treating sickle cell disease, as well as alternative embodiments being useful for discovering substances and formulations targeting dissolution of hemozoin, or preventing hemazoin formation, or micro-tubule polymerization or depolymerization among many possible applications.

Substances promoting dissolution of hemazoin provide a strategy to generate improved compounds and formulations that do not depend on continued hemoglobin degradation by the malarial parasite for generating toxic hematin and instead, or in addition, generate toxic hematin from already formed hemazoin. Such compounds and formulations may provide better treatment options with higher efficacy in combating malaria, particularly in already infected individuals. Such a screen is possible by detecting dissolution of hemazoin to yield hematin in the presence of a test compound or formulation over time. Moreover, the ready availability of small animal models of malaria enables rapid and routine further testing.

5.5.1.2 Inhibiting Uric Acid Crystal Deposits

The described exemplary method and system identifies compounds that inhibit formation of Uric acid crystal deposits that are a characteristic of gout. Notably, the described method and system are readily applicable to screen for compounds to treat calcium containing deposits of pseudogout. Both of these disease conditions are described in greater detail in §§ 3.2.1 and 3.2.4. The following illustrative description is directed to uric acid crystals of gout.

The method and system include generating an array of vessels containing test compounds such that each vessel contains a test compound aliquot, mixing the test compounds with urate saturated human plasma, increasing the supersaturation of urate in the mixture of human plasma and test compounds by decreasing the temperature, preferably gradually, and identifying test compounds in whose presence crystals fail to form. These vessels may be in the form of wells in a multi-well plate, drops on a suitable surface, or other suitable containers.

Urate saturated biological fluid ("USF"), wherein example biological fluids include human plasma, joint fluid, and other fluids in various compartments, can be prepared, for instance, by dissolving crystalline monosodium urate, e.g., obtained from Sigma Chemicals of St. Louis, Mo., with gentle agitation at 45° C. Preferably, USF is allowed to achieve equilibrium saturation with urate although it is possible to practice the invention without always ensuring such saturation. Undissolved Urate is removed by centrifuging to obtain USF as the supernatant. USF is dispensed into vessels suitable for monitoring for crystal precipitation and mixed with the test compounds placed in the vessels. The test compounds may advantageously be provided as an aqueous preparation.

Following mixing of test compounds and USF excess water is removed if desired. Then, the vessels are sealed or otherwise treated to reduce evaporative losses. Preferably, the vessels are maintained to reduce the likelihood of precipitation of crystals during the USF preparation, aliquoting and mixing steps, e.g., by preheating the receiving vessels. A reduction in temperature, preferably gradual, then induces urate crystallization. During the temperature decline the vessels are monitored, e.g., optically, for the appearance of crystals or lack thereof. To this end, the brightly birefringent urate crystals are susceptible to various monitoring methods including polarimeters and turbidity.

Vessels that fail to form crystalline precipitates or are delayed in forming of such precipitates are suitable for further screening since they are more likely to correspond to test compounds suitable for inhibiting formation of uric acid crystals. Thus, it is possible to monitor both crystallization and the rate of crystallization for evaluating various test compounds. Since nucleation is a stochastic and kinetic event, many identical compositions are tested to achieve a meaningful statistical estimate of changes therein. Preferably, the number of replicates reflect the underlying probability distribution to ensure that observed nucleation rate is reliable with a probability of preferably 66%, more preferably 99% and even more preferably 95%. Preferably, each set of test compounds are tested in at least four vessels, more preferably in twenty or more vessels and even more preferably in ten to twenty vessels.

Following identification of test compounds likely to be useful as inhibitors of uric acid crystal formation, they may be further tested in vivo. For instance, the availability of the urate oxidase deficient mouse, described by Wu et al. in the *Proceedings of the National Academy of Sciences USA* in volume 91 at pages 742–746, said reference incorporated herein in its entirety by reference, makes possible further evaluation of selected test compounds. This evaluation can include estimating safety, preliminary dosage and other parameters relating to each test compound. The urate oxidase deficient mouse exhibits enhanced mortality in the first four weeks of life (by 65%) and also shows signs of kidney damage in affected mice. Therefore, it is sensitive and rapid small animal model for evaluating compounds of interest in inhibiting uric acid crystal formation. The development of additional animal species and strains that lack urate oxidase would further extend the range of available animal model systems.

In addition, or alternatively to the use of the urate oxidase deficient mouse, the test compounds could be used in humans. To this end, the test compounds are advantageously chosen from the set of compounds that are known to be safe for administration to humans, e.g., such as those having passed Phase I clinical trials. In view of the results from the inhibition of uric acid crystal formation, these compounds maybe advantageously be tested for treating gout in clinical trials (Phase II or Phase III) to discover new uses for known compounds in an economical and safe manner or administered for such treatment. Other trials evaluating clinical efficacy such as pediatric trial, gender sensitive testing and testing directed to use of compounds in particular ethnic or geographically defined groups are also possible. Moreover, novel compounds for the treatment of uric acid crystal deposition are also identified by the described method and system a suitable choice of test compounds. To this end, libraries can be screened to identify useful compounds.

Thus, the invention encompasses high-throughput assays for identifying compounds, especially small molecules that can inhibit formation of uric acid crystals. Such compounds may be known compounds or novel compounds and may act to prevent or alleviate one or more disease symptoms.

5.5.1.3 Dissolving Uric Acid Crystal Deposits

In a manner similar to the method and system described in the preceding section for identifying compounds that inhibit uric acid crystal formation, it is possible to screen for compounds that aid in dissolving already deposited uric acid crystals. When the plasma level of urate is below saturation, uric acid crystals should dissolve. Increasing the rate of uric acid crystal dissolution is likely to determine the rate of alleviation of gout symptoms. Therefore, it is of interest to identify compounds that promote dissolution of uric acid crystals.

A system and method similar to that described in § 5.5.1.2 are useful for identifying such compounds. In a possible variant, vessels containing USP and test compounds are incubated at increasing temperatures to achieve subsaturation with respect to uric acid. Advantageously, prior to increasing the temperature, urate crystals are allowed to precipitate by lowering the temperature followed by mixing with the test compounds. Agitation of the subsaturated solution allows for an assessment of the rate of dissolution of crystals. Vessels corresponding to fast dissolving crystals are identified to further test the corresponding test compounds for modification of uric acid crystals including their habit, and activity, and safety in vivo.

As in the case of the system and method described in § 5.5.1.2, the urate oxidase mouse provides a useful model for evaluating safety, efficacy in vivo and dosage. Additional animal models are possible with uric acid crystals introduced ectopically into selected sites such as the subcutaneous pouch and the peritoneum. Test compounds so identified have utility as medicines, for instance as administered to patients receiving uric acid lowering therapies.

Thus, the invention encompasses high-throughput assays for identifying compounds, especially small molecules that can promote the dissolution of deposited uric acid crystals in the course of treating gout. Such compounds may be known compounds or novel compounds and may act to prevent or alleviate one or more disease symptoms. The invention also encompasses the use of such compounds identified in the assays to treat diseases.

5.5.1.4 Dissolving and/or Inhibiting Calcium Phosphate and Calcium Oxalate Deposits The method and system described in § 5.5.1.2 and are also useful for other disorders. In particular, preparation of supersaturated plasma preparation of Calcium Phosphate or Calcium Oxalate may be similar with optical monitoring of crystallization or precipitation.

Thus, the invention encompasses high-throughput assays for identifying compounds, especially small molecules that can inhibit the formation of or promote the dissolution of Calcium containing crystals and other types of crystals that otherwise result in a disease state. Such compounds may be known compounds or novel compounds and may act to prevent or alleviate one or more disease symptoms.

Although the present invention has been described in considerable detail with reference to certain preferred embodiments, other embodiments are possible. Therefore, the spirit and scope of the appended claims should not be limited to the description of the preferred embodiments contained herein. Modifications and variations of the invention described herein will be obvious to those skilled in the art from the foregoing detailed description and such modifications and variations are intended to come within the scope of the appended claims.

A number of references have been cited, the entire disclosures of which are incorporated herein by reference.

What is claimed is:

1. A method of screening an array of at least 96 samples to identify conditions, compounds, or compositions that inhibit or prevent transitions of physical state comprising:
   (a) preparing and identifying an array of at least 96 samples in tubes and support plates or in sample well plates and dispensing a liquid medium, a disease-causing substance comprising crystallized calcium oxalate in liquid form, salts of citric acid and one or more additional components into sample tubes or sample wells with an automated distribution mechanism, and wherein each sample differs with respect to the identity of one or more of the additional components;
   (b) processing one or more of the samples to induce crystallization, precipitation or deposition of the disease causing substance, said processing comprising the addition of one or more additional components;
   (c) analyzing the processed samples to detect the induction of said crystallization, precipitation or deposition using polarized light analysis and Raman spectroscopy; and
   (d) selecting those processed samples that exhibit inhibition or prevention of a transition in physical state.

2. The method of claim 1, comprising the addition of said samples to tubes in a support plate.

3. The method of claim 2, wherein said tubes are glass tubes and said support plate is a metal support plate.

4. The method of claim 1, comprising sealing said tubes with a cap.

5. The method of claim 4, wherein said cap is pierced with a standard syringe needle and fluid aspirated through the syringe tip to remove solvent from the sample.

6. The method of claim 1, wherein said array comprises at least 1000 samples.

7. The method of claim 1, further comprising the generation of a work list for instructing an automated distribution mechanism to prepare said array of samples.

8. The method of claim 1, wherein said sample contains less than 1 milligram of said disease-causing substance.

9. The method of claim 6, comprising the piercing of said cap and aspiration of medium from said samples.

10. The method of claim 1, wherein said one or more of the additional components the is a small molecule.

11. The method of claim 1, wherein said array comprises at least 1 sub-array.

12. The method of claim 1, wherein said array comprises at least 1 sub-array with at least 24 samples.

13. The method of claim 1, wherein the processed samples are analyzed to detect a solid or an absence of a solid.

14. The method of claim 13, wherein a detected solid is analyzed to determine if the solid is amorphous or crystalline.

15. The method of claim 1, wherein at least about 100 samples are screened per day.

16. The method of claim 1, wherein at least about 1000 samples are screened per day.

17. The method of claim 1, wherein said array comprises sub-arrays, and wherein an individual sample within a sub-array is subjected to processing methods that are different from the processing methods to which another sample within the sub-array is subjected.

18. The method of claim 17, wherein said individual sample is subjected to processing methods comprising adding one or more additional components.

19. The method of claim 1, wherein said array comprises sub-arrays, and wherein an individual sub-array is subjected to processing methods that are different from the processing methods to which another sub-array is subjected.

20. The method of claim 19, wherein said individual sub-array is subjected to processing methods comprising adding one or more additional components.

21. The method of claim 1, wherein the amount of said disease-causing substance in each sample is less than about 1 milligram.

22. The method of claim 1, wherein the amount of said disease-causing substance in each sample is less than about 100 micrograms.

23. The method of claim 1, wherein the amount of said disease-causing substance in each sample is less than about 100 nanograms.

24. The method of claim 1, wherein each sample has a total volume between 5–500 μl.

25. The method of claim 1, wherein each sample has a total volume between 10–200 μl.

* * * * *